(12) United States Patent
Eishingdrelo et al.

(10) Patent No.: US 7,432,361 B2
(45) Date of Patent: Oct. 7, 2008

(54) G PROTEIN-COUPLED RECEPTOR, GAVE10

(75) Inventors: Haifeng Eishingdrelo, Montville, NJ (US); Mohamad Ali Ardati, Basking Ridge, NJ (US); Jidong Cai, Whippany, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 438 days.

(21) Appl. No.: 10/491,376

(22) PCT Filed: Sep. 30, 2002

(86) PCT No.: PCT/US02/31045

§ 371 (c)(1),
(2), (4) Date: Jun. 7, 2004

(87) PCT Pub. No.: WO03/029413

PCT Pub. Date: Apr. 10, 2003

(65) Prior Publication Data

US 2004/0234993 A1 Nov. 25, 2004

Related U.S. Application Data

(60) Provisional application No. 60/325,591, filed on Oct. 1, 2001.

(51) Int. Cl.
*G01N 33/06* (2006.01)
*G01N 33/14* (2006.01)

(52) U.S. Cl. .................. 536/23.1; 536/24.3; 536/24.31

(58) Field of Classification Search ............... 536/23.1, 536/24.3, 24.31
See application file for complete search history.

(56) References Cited

U.S. PATENT DOCUMENTS

2002/0119493 A1* 8/2002 Glucksmann ............... 435/7.1

FOREIGN PATENT DOCUMENTS

EP  1 270 724  1/2003
EP  1 273 659  1/2003
EP  1 347 052  9/2003
WO  WO 02/10387  2/2002

OTHER PUBLICATIONS

GenBank Acc. No. AF275151, Chan, M.T.W., Rattus norvegicu androgen receptor-related apoptosis-associate protein CBL27 mRNA, Jul. 20, 2000, US National Library of Medicine, Bethesda, MD, accessed by PTO on Oct. 4, 2006.*
Alignment of Genbank Accession No. AF275151 (nucleotides 1-25) with nucleotides 73-97 of SEQ ID No. 1.*
Kennel, D. 1971, Principles and practices of nucleic acid hybridiaqtion, Prog Nucl Acid Res Mol Biol 11:259-301.*
GenBank Acc. No. J04617, Uetski, T, Human elongation factor EF-1-alpha gene, Nov. 7, 1994, US National Library of Medicine, Bethesda, MD, accessed by PTO on Oct. 4, 2006.*
Alignment of Genbank Accession No. J04617 (nucleotides 1522-1563) with nucleotides 9-49 of SEQ ID No. 1.*
Kremer, L et al., 1999, In vivo immunomodulation folloeing intradermal injection with DNA encoding IL18, Jour Immunol., 163:3226-3231.*
Alignment of Genbank Accession No. AX375233 (SEQ ID No. 23 of WO0210387) with SEQ ID No. 1.*
Alignment of SEQ ID No. 3 of US2002/0119493A1 with SEQ ID No. 2 of the instant application.*
U.S. Appl. No. 09/911,005, filed Jul. 23, 2001, Glucksmann.
Chen, Grace et al., Use of Constitutive G Protein-Coupled Receptor Activity for Drug Discovery, Molecular Pharmacology, (2000), vol. 57, pp. 125-134.
Pauwels, Petrus J. et al., Review: Aminio Acid Domains Involved in Constitutive Activation of G-Protein-Coupled Receptors, Molecular Neurobiology, (1998), vol. 17, pp. 109-135.
Takeda, Shegeki et al., Systematic search for G protein-coupled receptor genes from human genome database.

* cited by examiner

*Primary Examiner*—Valarie Bertoglio

(57) ABSTRACT

Novel GPCR GAVE10 polypeptides, proteins and nucleic acid molecules are provided. GAVE10, recombinant expression vectors, host cells incorporating GAVE10 expression vectors and non-human transgenic animals into which a GAVE10 gene has been introduced or disrupted are taught. Diagnostic, screening and therapeutic methods utilizing compositions of the invention also are provided.

5 Claims, 2 Drawing Sheets

```
CCTTAGACGTGGTTCAAAGTTTTTTTCTTCCTTTCAGGTGTCGTGAAAAGCTTGAATTCGGCGCGCCA
GATATCACACGTGCCAAGGGGCTGGCTCAGGAGAGCCTGGCCCCGCTGTCCCCACTGGGTGGAGA
CACCATGCACTTGGTCCACTTGTGCTCTTCAGCCAGGACACCAGACATGGTCCAAACCGCTGCAGG
GCTGGCTGCAGCAACTCCCTGACACTCAGGAAGGCCCAGGCTGGGCAGGCAATACCTGCTCCCAA
CAGCCATGCATGCCGGCTGCCGCTCCAGGACTCCCCTGTCCCCAGGACCAAGATGACGCCCAACA
GCACTGGCGAGGTGCCCAGCCCCATTCCCAAGGGGGCTTTGGGGCTCTCCCTGGCCCTGGCAAGC
CTCATCATCACCGCGAACCTGCTCCTAGCCCTGGGCATCGCCTGGGACCGCCGCCTGCGCAGCCC
ACCTGCTGGCTGCTTCTTCCTGAGCCTACTGCTGGCTGGGCTGCTCACGGGTCTGGCATGCCCAC
ATTGCCAGGGCTGTGGAACCAGAGTCGCCGGGGTTACTGGTCCTGCCTCCTCGTCTACTTGGCTCC
CAACTTCTCCTTCCTCTCCCTGCTTGCCAACCTCTTGCTGGTGCACGGGGAGCGCTACATGGCAGTC
CTGAGGCCACTCCAGCCCCTGGGAGCATTCGGCTGGCCCTGCTCCTCACCTGGGCTGGTCCCCT
GCTCTTTGCCAGTCTGCCCGCTCTGGGGTGGAACCACTGGACCCCTGTGCCAACTGCAGCTCCCA
GGCTATCTTCCCAGCCCCCTACCTGTACCTCGAAGTCTATGGGCTCCTGCTGCCCGCCGTGGGTGC
TGCTGCCTTCCTCTCTGTCCGCGTGCTGGCCACTGCCCACCGCCAGCTGCAGGACATCTGCCGGCT
GGAGCGGGCAGTGTGCCGCGATGAGCCCTCCGCCCTGGCCCGGGCCCTTACCTGGAGGCAGGCA
AGGGCACAGGCTGGAGCCATGCTGCTCTTCGGGCTGTCTGGGGGCCCTACGTGGCCACACTGCT
CCTCTCAGTCCTGGCCTATGAGCAGCGCCCGCCACTGGGGCCTGGGACACTGTTGTCCCTCCTCTC
CCTAGGAAGTGCCAGTGCAGCGGCAGTGCCCGTAGCCATGGGGCTGGGCGATCAGCGCTACACAG
CCCCCTGGAGGGCAGCCGCCCAAAGGTGCCTGCAGGGGCTGTGGGGAAGAGCCTCCCGGGACAG
TCCCGGCCCCAGCATTGCCTACCACCCAAGCAGCCAAAGCAGTGTCGACCTGGACTTGAACTAAAG
GAAGGGCCTCTGCTGACTCCTACCAGAGCATCCGTCCAGCTCAGCCATCCAGCCTGTCTCTACTGG
GCCCCACTTCTCTGGATCAGAGACCCTGCCTCTGTTTGACCCCGCACTGACTGAATAAAGCTCCTCT
GGCCGTTAAAAAAAAAAAAAAAAAAAAAAAAAAAAAAAAAAAAAAAAAAAAAAAACATTACCTCTTTCTC
CGCACCTGGCCTGCAGGCGGCCGCAGGTAAGCCAGCCCAGGCCTCGCCCTCCAGCTCAAGGCGG
GACAGGTGC
```

FIGURE 1

MTPNSTGEVPSPIPKGALGLSLALASLIITANLLLALGIAWDRRLRSPPAGCFFLSLLLAGLLTGLALPTLPGLWNQSRR
GYWSCLLVYLAPNFSFLSLLANLLLVHGERYMAVLRPLQPPGSIRLALLLTWAGPLLFASLPALGWNHWTPGANCSSQAI
FPAPYLYLEVYGLLLPAVGAAAFLSVRVLATAHRQLQDICRLERAVCRDEPSALARALTWRQARAQAGAMLLFGLCWGPY
VATLLLSVLAYEQRPPLGPGTLLSLLSLGSASAAAVPVAMGLGDQRYTAPWRAAAQRCLQGLWGRASRDSPGPSIAYHPS
SQSSVDLDLN

FIGURE 2

G PROTEIN-COUPLED RECEPTOR, GAVE10

BACKGROUND OF THE INVENTION

The G protein-coupled receptors (GPCRs) are a large family of integral membrane proteins that are involved in cellular signal transduction. GPCRs respond to a variety of extracellular signals, including neurotransmitters, hormones, odorants and light, and are capable of transducing signals so as to initiate a second messenger response within the cell. Many therapeutic drugs target GPCRs because those receptors mediate a wide variety of physiological responses, including inflammation, vasodilation, heart rate, bronchodilation, endocrine secretion and peristalsis.

GPCRs are characterized by extracellular domains, seven transmembrane domains and intracellular domains. Some of the functions the receptors perform, such as binding ligands and interacting with G proteins, are related to the presence of certain amino acids in critical positions. For example, a variety of studies have shown that differences in amino acid sequence in GPCRs account for differences in affinity to either a natural ligand or a small molecule agonist or antagonist. In other words, minor differences in sequence can account for different binding affinities and activities. (See, for example, Meng et al., J Bio Chem (1996) 271(50):32016-20; Burd et al., J Bio Chem (1998) 273(51):34488-95; and Hurley et al., J Neurochem (1999) 72(1):413-21). In particular, studies have shown that amino acid sequence differences in the third intracellular domain can result in different activities. Myburgh et al. found that alanine 261 of intracellular loop 3 of gonadotropin releasing hormone receptor is crucial for G protein coupling and receptor internalization (Biochem J (1998) 331(Part 3):893-6). Wonerow et al. studied the thyrotropin receptor and demonstrated that deletions in the third intracellular loop resulted in constitutive receptor activity (J Bio Chem (1998)273(14):7900-5).

In general, the action of the binding of an endogenous ligand to a receptor results in a change in the conformation of the intracellular domain(s) of the receptor allowing for coupling between the intracellular domain(s) and an intracellular component, a G-protein. Several G proteins exist, such as $G_q$, $G_s$, $G_i$, $G_z$, and $G_o$ (see, e.g. Dessauer et al., Clin Sci (Colch) (1996) 91(5):527-37). The IC-3 loop as well as the carboxy terminus of the receptor interact with the G proteins (Pauwels et al., Mol Neurobiol (1998) 17(1-3):109-135 and Wonerow et. al., supra). Some GPCRs are "promiscuous" with respect to G proteins, i.e., a GPCR can interact with more than one G protein (see, e.g., Kenakin, Life Sciences (1988) 43:1095).

Ligand activated GPCR coupling with G protein begins a signaling cascade process (referred to as "signal transduction"). Such signal transduction ultimately results in cellular activation or cellular inhibition.

GPCRs exist in the cell membrane in equilibrium between two different conformations: an "inactive" and an "active" state. A receptor in an inactive state is unable to link to the intracellular signaling transduction pathway to produce a biological response (exceptions exist, such as during over-expression of receptor in transduced cells, see e.g., www.creighton.edu/Pharmacology/inverse.htm). Modulation of the conformation to the active state allows linkage to the transduction pathway (via the G protein) and produces a biological response. Agonists bind and make the active conformation much more likely. However, sometimes, if there is already a considerable response in the absence of any agonist, such receptors are said to be constitutively active (i.e., already in an active conformation or ligand independent or autonomous active state). When agonists are added to such systems, an enhanced response routinely is observed. However, when a classical antagonist is added, binding by such molecules produces no effect. On the other hand, some antagonists cause an inhibition of the constitutive activity of the receptor, suggesting that the latter class of drugs technically are not antagonists but are agonists with negative intrinsic activity. Those drugs are called inverse agonists, (www.creighton.edu/Pharmacology/inverse.htm).

Traditional study of receptors has proceeded from the assumption that the endogenous ligand first be identified before discovery could move forward to identify antagonists and other receptor effector molecules. Even where antagonists might have been discovered first, the dogmatic response was to identify the endogenous ligand (WO 00/22131). However, as the active state is the most useful for assay screening purposes, obtaining such constitutive receptors, especially GPCRs, would allow for the facile isolation of agonists, partial, agonists, inverse agonists and antagonists in the absence of information concerning endogenous ligands. Moreover, in diseases that result from disorders of receptor activity, drugs that cause inhibition of constitutive activity, or more specifically, reduce the effective activated receptor concentration, could be discovered more readily by assays using receptors in the autonomous active state. For example, as receptors that may be transfected into patients to treat disease, the activity of such receptors may be fine-tuned with inverse agonists discovered by such assays.

Diseases such as asthma, chronic obstructive pulmonary disease (COPD) and rheumatoid arthritis (RA) generally are considered to have an inflammatory etiology involving T helper cells, monocyte-macrophages and eosinophils. Current anti-inflammatory therapy with corticosteroids is effective in asthma but is associated with metabolic and endocrine side effects. The same is possibly true for inhaled formulations that can be absorbed through lung or nasal mucosa. Satisfactory oral therapies for RA or COPD currently are lacking.

Eosinophils mediate much of the airway dysfunction in allergy and asthma. Interleukin-5 (IL-5) is an eosinophil growth and activating cytokine. Studies have shown IL-5 to be necessary for tissue eosinophilia and for eosinophil-mediated tissue damage resulting in airway hyperresponsiveness (Chang et al., J Allergy Clin Immunol (1996) 98(5 pt 1):922-931 and Duez et al., Am J Respir Crit Care Med (2000) 161(1):200-206). IL-5 is made by T-helper-2 cells (Th2) following allergen (e.g. house dust mite antigen) exposure in atopic asthma.

RA is believed to result from accumulation of activated macrophages in the affected synovium. Interferon γ (IFNγ) is a T-helper-1 (Th 1) cell-derived cytokine with numerous proinflammatory properties. It is the most potent macrophage activating cytokine and induces MHC class II gene transcription contributing to a dendritic cell-like phenotype.

Lipopolysaccharide (LPS) is a component of gram-negative bacterial cell walls that elicits inflammatory responses, including tumor necrosis factor α (TNFα) release. The efficacy of intravenous anti-TNFα therapy in RA has been demonstrated in the clinic. COPD is thought also to result from macrophage accumulation in the lung, the macrophages produce neutrophil chemoattractants (e.g., IL-8: de Boer et al., J Pathol (2000) 190(5):619-626). Both macrophages and neutrophils release cathepsins that cause degradation of the alveolar wall. It is believed that lung epithelium can be an important source for inflammatory cell chemoattractants and other inflammatory cell-activating agents (see, for example, Thomas et al., J Virol (2000) 74(18):8425-8433; Lamkhioued et al., Am J Respir Crit Care Med (2000) 162(2 Pt. 1):723-732; and Sekiya et al., J Immunol (2000) 165(4):2205-2213).

Given the role GPCRs have in disease and the ability to treat diseases by modulating the activity of GPCRs, identification and characterization of previously unknown GPCRs can provide for the development of new compositions and methods for treating disease states that involve the activity of a GPCR. The instant invention identifies and characterizes the expression of a novel constitutively active GPCR, GAVE10, and provides compositions and methods for applying the discovery to the identification and treatment of related diseases. For example, GAVE10 is induced by LPS in THP-1 cells (a monocyte leukemic cell line) and is expressed at higher levels in synovia of patients with rheumatoid arthritis as compared to synovia of normals. GAVE10 expression is up-regulated by γ-interferon in macrophages.

SUMMARY OF THE INVENTION

The instant invention relates to a newly identified G protein-coupled receptor, designated herein as GAVE10. In one embodiment, GAVE10 is derived from an intronless structural gene encoding about 330 amino acids as set forth in SEQ ID NO:2. In a related aspect, a polynucleotide as set forth in SEQ ID NO:1 is contemplated, corresponding to a nucleic acid comprising about 1586 base pairs (bp).

In another aspect, the invention relates to isolated nucleic acids selected from the group consisting of an isolated nucleic acid that encodes a vertebrate protein of amino acids as set forth in SEQ ID NO:2, variants, mutations and fragments thereof that retain a GAVE10 activity and an isolated nucleic acid that comprises a nucleotide sequence as set forth in SEQ ID NO:1, variants, mutations and fragments thereof that encode a polypeptide with a GAVE10 activity. Further, the invention relates to nucleic acid hybridization probes and complementary fragments that bind to SEQ ID NO:1 or hybridization probes and complementary fragments that bind to nucleic acids that encode the amino acid sequence as set forth in SEQ ID NO:2. Further, the invention relates to nucleic acids having about 30% to about 99% identity to SEQ ID NO:1, including nucleic acids having about 30% to about 99% identity to isolated nucleic acids encoding an amino acid sequence as set forth in SEQ ID NO:2. In a related aspect, the oligonucleotides comprise at least 8 nucleotides and methods of hybridizing are contemplated comprising the steps of contacting the complementary oligonucleotide with a nucleic acid comprising the nucleotides as set forth in SEQ ID NO:1, or substantial equivalent thereof, under conditions that permit hybridization of the complement with the nucleic acid. Further, complementary fragments may serve as anti-sense oligonucleotides for methods of inhibiting the expression of GAVE10, in vivo and in vitro. Such methods may comprise the steps of providing an oligonucleotide sequence consisting of the complement of the nucleotides as set forth in SEQ ID NO:1, providing a human cell comprising an mRNA compromising the sequence of nucleotides as set forth in SEQ ID NO:1 and introducing the oligonucleotide into the cell, where the expression of GAVE10 is inhibited by mechanisms that include inhibition of translation, triple helix formation and/or nuclease activation leading to degradation of mRNA in the cell.

The invention also relates to isolated polypeptides selected from the group consisting of purified polypeptides of amino acid sequence as set forth in SEQ ID NO:2, variants, mutations and fragments thereof and purified polypeptides having additional amino acid residues that provide a functional property of GAVE10.

The invention further relates to the nucleic acids operably linked to an expression control element, including vectors comprising the isolated nucleic acids. The invention further relates to cultured cells transfected or transformed to comprise the nucleic acids of the invention. The invention further relates to methods for producing a polypeptide comprising the steps of growing transformed cells comprising the nucleic acids of the invention, permitting expression under an expression control element and purifying the polypeptide from the cell or medium in that the cell was cultured.

A further aspect of the invention includes an isolated antibody that binds to a polypeptide of the invention, including monoclonal and polyclonal antibodies. Further, in a related aspect, methods of producing antibodies and methods for treating GAVE10-related diseases with an antibody that binds to GAVE10 are disclosed. The antibody also can be used to identify molecules that activate GAVE10 without binding ligand.

An additional aspect of the invention includes methods, for diagnostic purposes, for ascertaining the presence or absence of GAVE10 in a biological and/or tissue sample. In another embodiment, exposure to LPS can be monitored or ascertained. In another aspect of the invention, therapeutic methods are disclosed for modulating GAVE10 signal transduction, including administration of peptides, agonists, antagonists, inverse agonists and/or antibody to a patient in need thereof.

In another aspect of the invention, methods are disclosed for identifying modulators of GAVE10 comprising the steps of providing a chemical moiety, providing a cell expressing GAVE10 and determining whether the chemical moiety modulates the signaling activity of GAVE10, including whether such modulation occurs in the presence or absence of an endogenous ligand. In a related aspect, the chemical moieties can include, but are not limited to, peptides, antibodies, agonists, inverse agonists and antagonists.

In another aspect, the invention features a method for determining whether a candidate compound is an inverse agonist, where said candidate is exposed to the constitutive receptor in the absence of endogenous ligand, classical agonist or classical antagonist and such constitutive activity is inhibited by said inverse agonist.

Another aspect of the invention includes therapeutic compositions, where such compositions include nucleic acids, antibodies, polypeptides, agonists, inverse agonists and antagonists. Further, methods of the invention also include methods of treating disease states and modulating GAVE10 signaling activity by administering such therapeutic compositions to a patient in need thereof.

Those and other aspects of the invention will become evident on reference to the following detailed description and attached drawings. In addition, various references are set forth below that describe in more detail certain procedures or compositions. Each of the references hereby is incorporated herein by reference as if each were individually noted for incorporation.

BRIEF DESCRIPTION OF THE DRAWINGS

FIG. 1 is a DNA sequence for hGAVE10 (SEQ ID NO:1).
FIG. 2 is the corresponding amino acid sequence for hGAVE10 (SEQ ID NO:2).

DETAILED DESCRIPTION OF THE INVENTION

The instant invention is based on the discovery of a cDNA molecule encoding human GAVE10, a member of the G protein-coupled receptor superfamily.

The term "agonist" as used herein means moieties (e.g., but not limited to ligands and candidate compounds) that activate the intracellular response when bound to the receptor, or enhance GTP binding to membranes.

The term "partial agonist" as used herein means moieties (e.g., but not limited to ligands and candidate compounds) that activate the intracellular response when bound to the receptor to a lesser degree/extent then do agonists, or enhance GTP binding to membranes to a lesser degree/extent than do agonists.

The term "antagonist" as used herein means moities (e.g., but not limited to ligands and candidate compounds) that competitively bind to the receptor at the same site as does an agonist. However, an antagonist does not activate the intracellular response initiated by the active form of the receptor and thereby can inhibit the intracellular responses by agonists or partial agonists. In a related aspect, antagonists do not diminish the baseline intracellular response in the absence of an agonist or partial agonist.

The term "candidate compound" herein means a moiety (e.g., but not limited to a chemical compound) that is amenable to a screening technique. In one embodiment, the term does not include compounds that were publicly known to be compounds selected from the group consisting of agonist, partial agonist, inverse agonist or antagonist. Those compounds were identified by traditional drug discovery processes involving identification of an endogenous ligand specific for a receptor, and/or screening of candidate compounds against a receptor wherein such a screening requires a competitive assay to assess efficacy.

The term "constitutively activated receptor" or "autonomously active receptor," herein used interchangeably, means a receptor subject to activation in the absence of ligand.

In a related aspect, such constitutively active receptors can be endogenous (e.g., GAVE10) or non-endogenous; i.e., GPCRs can be modified by recombinant means to produce mutant constitutive forms of wild-type GPCRs (e.g., see EP 1071701; WO 00/22129; WO 00/22131; and U.S. Pat. Nos. 6,150,393 and 6,140,509, herein incorporated by reference).

The term "constitutive receptor activation" herein means stabilization of a receptor in the active state by means other than binding of the receptor with the endogenous ligand or chemical equivalent thereof.

The term "inverse agonist" herein means moieties (e.g., but not limited to ligand and candidate compound) that bind to a constitutively active receptor and that inhibit the baseline intracellular response. The baseline response is initiated by the active form of the receptor below the normal base level of activity that is observed in the absence of agonists or partial agonists, or decrease of GTP binding to membranes.

The term "ligand" herein means a moiety that binds to another molecule, wherein said moiety is, such as, but not limited to, a hormone or a neurotransmitter, and further wherein said moiety which stereoselectively binds to a receptor.

A nucleotide sequence encoding a human GAVE10 protein is shown in FIG. 1 (SEQ ID NO:1). An amino acid sequence of GAVE10 protein is shown in FIG. 1 (SEQ ID NO:2).

The GAVE10 cDNA of FIG. 1 (SEQ ID NO:1), that is approximately 1586 nucleotides long, including untranslated regions, encodes an intronless protein having a length of approximately 330 amino acids with a molecular weight of about 35 kD.

Using a Northern blot assay, a GAVE10 mRNA transcript of approximately 1.8 kb is expressed in certain tissues. GAVE10, by RT-PCR, was shown to be expressed in THP-1 exposed to LPS. The receptor in transfected HEK293 cells also shows constitutive activation in the absence of agonist. Further, Northern blot results indicated that GAVE10 expression is not detected in brain, skeletal muscle or pancreas. In contrast, GAVE10 is expressed in placenta, liver and kidney, and weakly expressed in the heart. In a related aspect, TaqMan RT-PCR experiments were carried out to further evaluate GAVE10 expression. Results from a tissue panel indicated that GAVE10 showed expression in spleen, and also in kidney, heart, thymus and liver. GAVE10 expression also was elevated in activated vascular endothelial cells, activated macrophages such as by exposure to $IFN_\gamma$ and activated CD19 cells. GAVE10 expression was elevated in fibroblast-like synoviocytes activated by exposure to IL-1 or TNF. GAVE10 expression is elevated in synovial tissue from patients having rheumatoid arthritis or osteoarthritis.

The term "family," when referring to the protein and nucleic acid molecules of the invention, is intended to mean two or more proteins or nucleic acid molecules having a seemingly common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that second protein. Members of a family also may have common functional characteristics.

In one embodiment, a GAVE10 protein includes a third intracellular loop domain having at least about 65%, preferably at least about 75% and more preferably about 85%, 95%, 98% or 100% amino acid sequence identity to the third intracellular loop domain of SEQ ID NO:2 having a GAVE10 activity.

The term "equivalent amino acid residues" herein means the amino acids occupy substantially the same position within a protein sequence when two or more sequences are aligned for analysis. Preferred GAVE10 polypeptides of the instant invention have an amino acid sequence sufficiently identical to the third intracellular loop domain amino acid sequence of SEQ ID NO:2. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence. The first and second amino acid or nucleotide sequences have a common structural domain and/or common functional activity. For example, amino acid or nucleotide sequences that contain a common structural domain having about 55% identity, preferably 65% identity, more preferably 75%, 85%, 95% or 98% identity with GAVE10 activity are defined herein as sufficiently identical.

Other domains of interest include, but are not limited to, the transmembrane (TM) domains (TM1 from about amino acid residue 15 to about 39; TM2 from about amino acid residue 50 to about 71; TM3 from about amino acid residue 84 to about 107; TM4 from about amino acid residue 124 to about 144; TM5 from about amino acid residue 159 to about 192; TM6 from about 227 to about 250; and TM7 about amino acid residue 259 to about 282 as set forth in SEQ ID NO:2), cytoplasmic (intracellular) (IC) domains (IC1 from about amino acid residue 40 to about 49; IC2 from about amino acid residue 108 to about 123; IC3 from about amino acid residue 193 to about 226; and IC4 from about amino acid 283 to about 330 as set forth in SEQ ID NO:2) and extracellular (EC) domains (EC1 from about amino acid residue 1 to about 4; EC2 from about amino acid residue 72 to about 83; EC3 from about amino acid 145 to about 158; and EC4 from about amino acid residue 251 to about 258 as set forth in SEQ ID NO:2). In a related aspect, domains of interest also include, but are not limited to, consensus glycosylation sites, lipid binding sites and phosphorylation sites. Asparagine residues are located in the N-terminus and the EC2 and EC3 loops. Kinase phosphorylation sites such as, serines, are found in IC3 and the C-terminus. GAVE10 also possesses the ERY motif instead of the typical DRY motif downstream from TM3.

As used interchangeably herein, a "GAVE10 activity", "biological activity of GAVE10" or "functional activity of GAVE10", refers to an activity exerted by a GAVE10 protein, polypeptide or nucleic acid molecule on a GAVE10 responsive cell as determined in vivo or in vitro, according to standard techniques. A GAVE10 activity can be a direct activity, such as an association with or an enzymatic activity on a second protein or an indirect activity, such as a cellular signaling activity mediated by interaction of the GAVE10 protein with a second protein. In a preferred embodiment, a GAVE10 activity includes at least one or more of the following activities: (i) the ability to interact with proteins in the GAVE10 signaling pathway; (ii) the ability to interact with a GAVE10 ligand; and (iii) the ability to interact with an intracellular target protein.

Accordingly, another embodiment of the invention features isolated GAVE10 proteins and polypeptides having a GAVE10 activity.

Various aspects of the invention are described in further detail in the following subsections.

Isolated Nucleic Acid Molecules

One aspect of the invention pertains to isolated nucleic acid molecules that encode GAVE10 proteins or biologically active portions thereof. The nucleic acid molecules or portions thereof are sufficient for use as hybridization probes to identify GAVE10-encoding nucleic acids (e.g., GAVE10 mRNA). Relevant nucleic acids also can be used as PCR primers for the amplification or mutation of GAVE10 nucleic acid molecules. As used herein, the term "nucleic acid molecule" is intended to include DNA molecules (e.g., cDNA or genomic DNA) and RNA molecules (e.g., mRNA) and analogs of DNA or RNA generated using nucleotide analogs. The nucleic acid molecule can be single-stranded or double-stranded, but preferably is double-stranded DNA.

An "isolated" nucleic acid molecule is one that is separated from other nucleic acid molecules present in the natural source of the nucleic acid. Preferably, an "isolated" nucleic acid is free of sequences that naturally flank the nucleic acid encoding GAVE10 (i.e., sequences located at the 5' and 3' ends of the nucleic acid) in the genomic DNA of the organism from that the nucleic acid is derived. For example, as GAVE10 is located on human chromosome 12 (i.e., 143 megabases), in various embodiments, the isolated GAVE10 nucleic acid molecule can contain less than about 5 kb, 4 kb, 3 kb, 2 kb, 1 kb, 0.5 kb or 0.1 kb of nucleotide sequences that naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques or substantially free of chemical precursors or other chemicals when synthesized chemically.

A nucleic acid molecule of the instant invention, e.g., a nucleic acid molecule having the nucleotide sequence of SEQ ID NO:1 or a fragment or complement of any of that nucleotide sequence, can be isolated using standard molecular biology techniques and the sequence information provided herein. Using all or a portion of the nucleic acid sequence of SEQ ID NO:1 as a hybridization probe, GAVE10 nucleic acid molecules can be isolated using standard hybridization and cloning techniques (e.g., as described in Sambrook et al., eds., Molecular Cloning: A Laboratory Manual, $2^{nd}$ ed., Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. For example, such primers can comprise, but are not limited to 5'-ATGACGCCCAA-CAGCACT-3' (SEQ ID NO:3) and 5'-TTAGTTCAAGTC-CAGGTC-3' (SEQ ID NO:4). The nucleic acid so amplified can be cloned into an appropriate vector and characterized by DNA sequence analysis. Furthermore, oligonucleotides corresponding to GAVE10 nucleotide sequences can be prepared by standard synthetic techniques, e.g., using an automated DNA synthesizer.

In another preferred embodiment, an isolated nucleic acid molecule of the invention comprises a nucleic acid molecule that is a complement of the nucleotide sequence shown in SEQ ID NO:1 or a GAVE10-specific portion thereof. A nucleic acid molecule that is complementary to a given nucleotide sequence is one that is sufficiently complementary to the given nucleotide sequence to hybridize with the given nucleotide sequence thereby to form an isolatable or detectable duplex.

Moreover, the nucleic acid molecule of the invention can comprise only a portion of a nucleic acid sequence encoding GAVE10, for example, a fragment that can be used as a probe or primer or a fragment encoding a biologically active portion of GAVE10. For example, such a fragment can comprise, but is not limited to, a region encoding amino acid residues about 1 to about 14 of SEQ ID NO:2. The nucleotide sequence determined from the cloning of the human GAVE10 gene allows for the generation of probes and primers for identifying and/or cloning GAVE10 homologues in other cell types, e.g., from other tissues, as well as GAVE10 homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1 or of a naturally occurring mutant of SEQ ID NO:1. Probes based on the human GAVE10 nucleotide sequence can be used to detect transcripts or genomic sequences encoding the similar or identical proteins. The probe may comprise a label group attached thereto, e.g., a radioisotope, a fluorescent compound, an enzyme or an enzyme cofactor. Such probes can be used as part of a diagnostic test kit for identifying cells or tissues that do not express properly GAVE10 protein. For example, that can be accomplished by measuring levels of a GAVE10-encoding nucleic acid in a sample of cells from a subject, e.g., detecting GAVE10 mRNA levels or determining whether a genomic GAVE10 gene has been mutated or deleted.

A nucleic acid fragment encoding a "biologically active portion of GAVE10" can be prepared by isolating a portion of SEQ ID NO:1 that encodes a polypeptide having a GAVE10 biological activity, expressing the encoded portion of GAVE10 protein (e.g., by recombinant expression in vitro) and assessing the activity of the encoded portion of GAVE10. For example, a nucleic acid fragment encoding a biologically active portion of GAVE10 includes a third intracellular loop domain, e.g., amino acid residues from about 202 to about 219 as set forth in SEQ ID NO:2. The invention further encompasses nucleic acid molecules that differ from the nucleotide sequence of SEQ ID NO:1 due to degeneracy of the genetic code and thus encode the same GAVE10 protein as that encoded by the nucleotide sequence shown in SEQ ID NO:1.

In addition to the human GAVE10 nucleotide sequence shown in SEQ ID NO:1, it will be appreciated by those skilled in the art that DNA sequence polymorphisms that lead to changes in the amino acid sequences of GAVE10 may exist within a population (e.g., the human population). Such genetic polymorphism in the GAVE10 gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding a GAVE10 protein, preferably a mammalian GAVE10 protein. As used herein, the phrase "allelic variant" refers to a nucleotide sequence that occurs at a GAVE10 locus or to a polypeptide encoded by the nucleotide sequence. Alternative alleles can be identified by sequencing the gene of interest in a number of different individuals. That can be carried out readily by using hybridization probes to identify the same genetic locus in a variety of individuals. Any and all such nucleotide variations and resulting amino acid polymorphisms or variations in GAVE10 that are the result of natural allelic variation and that do not alter the functional activity of GAVE10 are intended to be within the scope of the invention.

Moreover, nucleic acid molecules encoding GAVE10 proteins from other species (GAVE10 homologues) with a nucleotide sequence that differs from that of a human GAVE10, are intended to be within the scope of the invention. Nucleic acid molecules corresponding to natural allelic variants and homologues of the GAVE10 cDNA of the invention can be isolated based on identity with the human GAVE10 nucleic acids disclosed herein using the human cDNA or a portion thereof, as a hybridization probe according to standard hybridization techniques under stringent hybridization conditions.

Accordingly, in another embodiment, an isolated nucleic acid molecule of the invention is at least 300, 325, 350, 375, 400, 425, 450, 500, 550, 600, 650, 700, 800, 900, 1000 or 1100 nucleotides in length and hybridizes under stringent conditions to the nucleic acid molecule comprising the nucleotide sequence, preferably the coding sequence, of SEQ ID NO:1 or a complement thereof.

As used herein, the term "hybridizes under stringent conditions" is intended to describe conditions for hybridization and washing under that nucleotide sequences at least 55%, 60%, 65%, 70% and preferably 75% or more complementary to each other typically remain hybridized. Such stringent conditions are known to those skilled in the art and can be found in "Current Protocols in Molecular Biology", John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to the sequence of SEQ ID NO:1 or the complement thereof corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein). The skilled artisan will appreciate that the conditions may be modified in view of sequence-specific variables (e.g., length, G-C richness etc.).

The invention contemplates encompassing nucleic acid fragments of GAVE10 that are diagnostic of GAVE10-like molecules that have similar properties. The diagnostic fragments can arise from any portion of the GAVE10 gene including flanking sequences. The fragments can be used as probe of a library practicing known methods. The fragments can be made by known methods.

In addition to naturally-occurring allelic variants of the GAVE10 sequence that may exist in the population, the skilled artisan will further appreciate that changes can be introduced by mutation into the nucleotide sequence of SEQ ID NO:1, thereby leading to changes in the amino acid sequence of the encoded GAVE10 protein, without substantially altering the biological activity of the GAVE10 protein. For example, one can make nucleotide substitutions leading to amino acid substitutions at "non-essential" amino acid residues. A "non-essential" amino acid residue is a residue that can be altered from the wild type sequence of GAVE10 (e.g., the sequence of SEQ ID NO:2) without substantially altering the biological activity. An "essential" amino acid residue is one required for substantial biological activity. For example, amino acid residues that are not conserved or only semi-conserved among GAVE10 of various species may be non-essential for activity and thus would be likely targets of alteration. Alternatively, amino acid residues that are conserved among the GAVE10 proteins of various species may be essential for activity and thus would not be likely targets for alteration.

Accordingly, another aspect of the invention pertains to nucleic acid molecules encoding GAVE10 proteins that contain changes in amino acid residues that are not essential for activity. Such GAVE10 proteins differ in amino acid sequence from SEQ ID NO:2 yet retain biological activity. In one embodiment, the isolated nucleic acid molecule includes a nucleotide sequence encoding a protein that includes an amino acid sequence that is at least about 55% identical, 65%, 75%, 85%, 95%, 98%, 99% or 100% identical to the amino acid sequence of SEQ ID NO:2.

An isolated nucleic acid molecule encoding a GAVE10 protein having a sequence that differs from that of SEQ ID NO:2 can be created by introducing one or more nucleotide substitutions, additions or deletions into the nucleotide sequence of SEQ ID NO:1 such that one or more amino acid substitutions, additions or deletions are introduced into the encoded protein.

Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in that the amino acid residue is replaced with an amino acid residue having a similar side chain. Families of amino acid residues having similar side chains are defined in the art. The families include amino acids with basic side chains (e.g., lysine, arginine and histidine), acidic side chains (e.g., aspartic acid and glutamic acid), uncharged polar side chains (e.g., glycine, asparagine, glutamine, serine, threonine, tyrosine and cysteine), nonpolar side chains (e.g., alanine, valine, leucine, isoleucine, proline, phenylalanine, methionine and tryptophan), beta-branched side chains (e.g., threonine, valine and isoleucine) and aromatic side chains (e.g., tyrosine, phenylalanine, tryptophan and histidine). Thus, a predicted non-essential amino acid residue in GAVE10 preferably is replaced with another amino acid residue from the same side chain family. Alternatively, mutations can be introduced randomly along all or part of a GAVE10 coding sequence, such as by saturation mutagenesis, and the resultant mutants can be screened for GAVE10 biological activity to identify mutants that retain activity. Following mutagenesis, the encoded protein can be expressed recombinantly and the activity of the protein can be determined.

In a preferred embodiment, a mutant GAVE10 protein can be assayed for: (1) the ability to form protein:protein interactions with proteins in the GAVE10 signaling pathway; (2) the ability to bind a GAVE10 ligand; or (3) the ability to bind to an intracellular target protein. In yet another preferred embodiment, a mutant GAVE10 can be assayed for the ability to modulate cellular proliferation or cellular differentiation.

The instant invention encompasses antisense nucleic acid molecules, i.e., molecules that are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire GAVE10 coding strand or to only a portion thereof, e.g., all or part of the protein coding region (or open reading frame). An antisense nucleic acid molecule can be antisense to a noncoding region of the coding strand of a nucleotide sequence encoding GAVE10. The noncoding regions ("5' and 3' untranslated regions") are the 5' and 3' sequences that flank the coding region and are not translated into amino acids.

Given the coding strand sequences encoding GAVE10 disclosed herein (e.g., SEQ ID NO:1), antisense nucleic acids of the invention can be designed according to the rules of Watson & Crick base pairing. The antisense nucleic acid molecule can be complementary to the entire coding region of GAVE10 mRNA, but more preferably is an oligonucleotide that is antisense to only a portion of the coding or noncoding region of GAVE10 mRNA. For example, the antisense oligonucleotide can be complementary to the region surrounding the translation start site of GAVE10 mRNA. For example, an oligonucleotide having the sequence 5'-CTGTTGGGCGT-CATCTTGGTC-3' (SEQ ID NO:5). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be synthesized chemically using naturally occurring nucleotides or variously modified nucleotides designed to increase the biological stability of the molecules or to increase the physical stability of the duplex formed between the antisense and sense nucleic acids, e.g., phosphorothioate derivatives, phosphonate derivatives and acridine-substituted nucleotides can be used.

Examples of modified nucleotides that can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, β-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, β-D-mannosylqueosine, 5-methoxycarboxymethyluracil, 5-methoxyuracil, 2-methylthio-$N^6$-isopentenyladenine, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil and 2,6-diaminopurine. Alternatively, the antisense nucleic acid can be produced biologically using an expression vector into that a nucleic acid has been subcloned in an antisense orientation (i.e., RNA transcribed from the inserted nucleic acid will be of an antisense orientation to a target nucleic acid of interest).

The antisense nucleic acid molecules of the invention typically are administered to a subject or generated in situ so as to hybridize with or bind to cellular mRNA and/or genomic DNA encoding a GAVE10 protein thereby to inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix, or to a regulatory region of GAVE10.

An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that the molecules specifically bind to receptors or antigens expressed on a selected cell surface, e.g., by linking the antisense nucleic acid molecules to peptides or antibodies that bind to cell surface receptors or antigens. The antisense nucleic acid molecules also can be delivered to cells using the vectors described herein. To achieve sufficient intracelluar concentrations of the antisense molecules, vector constructs in that the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in that the strands run parallel to each other (Gaultier et al., Nucleic Acids Res (1987)15:6625-6641). The antisense nucleic acid molecule also can comprise a methylribonucleotide (Inoue et al., Nucleic Acids Res (1987) 15:6131-6148) or a chimeric RNA-DNA analogue (Inoue et al., FEBS Lett (1987) 215:327-330).

The invention also encompasses ribozymes. Ribozymes are catalytic RNA molecules with ribonuclease activity that are capable of cleaving a single-stranded nucleic acid, such as an mRNA, to that the ribozyme is hybridized. Thus, ribozymes (e.g., hammerhead ribozymes (described in Haselhoff et al., Nature (1988) 334:585-591)) can be used to cleave catalytically GAVE10 mRNA transcripts thereby to inhibit translation of GAVE10 mRNA. A ribozyme having specificity for a GAVE10-encoding nucleic acid can be designed based on the nucleotide sequence of a GAVE10 cDNA disclosed herein (e.g., SEQ ID NO:1). For example, a derivative of a Tetrahymena L-19 IVS RNA can be constructed in that the nucleotide sequence of the active site is complementary to the nucleotide sequence to be cleaved in a GAVE10-encoding mRNA, see, e.g., U.S. Pat. Nos. 4,987,071 and 5,116,742. Alternatively, GAVE10 mRNA can be used to select a catalytic RNA having a specific ribonuclease activity from a pool of RNA molecules, see, e.g., Bartel et al., Science (1993) 261:1411-1418.

The invention also encompasses nucleic acid molecules that form triple helical structures. For example, GAVE10 gene expression can be inhibited by targeting nucleotide sequences complementary to the regulatory region of the GAVE10 (e.g., the GAVE10 promoter and/or enhancers) to form triple helical structures that prevent transcription of the GAVE10 gene in target cells, see generally, Helene, Anticancer Drug Des (1991) 6(6):569; Helene Ann NY Acad Sci (1992) 660:27; and Maher, Bioassays (1992) 14(12):807.

In preferred embodiments, the nucleic acid molecules of the invention can be modified at the base moiety, sugar moiety or phosphate backbone to improve, e.g., the stability, hybridization or solubility of, the molecule. For example, the deoxyribose phosphate backbone of the nucleic acids can be modified to generate peptide nucleic acids (see Hyrup et al., Bioorganic & Medicinal Chemistry (1996) 4:5). As used herein, the terms "peptide nucleic acids" or "PNAs" refer to nucleic acid mimics, e.g., DNA mimics, in that the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al., Proc Natl Acad Sci USA (1996) 93:14670.

PNAs of GAVE10 can be used in therapeutic and diagnostic applications. For example, PNAs can be used as antisense or antigene agents for sequence-specific modulation of gene expression by, e.g., inducing transcription or translation arrest or inhibiting replication. PNAs of GAVE10 also can be used. For example, a PNA can be used in the analysis of single base pair mutations in a gene by, e.g., PNA-directed PCR clamping; as artificial restriction enzymes when used in combination with other enzymes, e.g., S1 nucleases (Hyrup et al. (1996) supra) or as probes or primers for DNA sequence and hybridization (Hyrup et al. (1996) supra; Perry-O'Keefe et al. (1996) supra).

In another embodiment, PNAs of GAVE10 can be modified, e.g., to enhance stability, specificity or cellular uptake, by attaching lipophilic or other helper groups to the PNA, by the formation of PNA-DNA chimeras or by the use of liposomes or other techniques of drug delivery known in the art. The synthesis of PNA-DNA chimeras can be performed as described in Hyrup et al. (1996) supra, Finn et al., Nucleic Acids Res (1996) 24(17):3357-63, Mag et al., Nucleic Acids Res (1989) 17:5973; and Peterser et al., Bioorganic Med Chem Lett (1975) 5:1119.

Isolated GAVE10 Proteins and Anti-GAVE10 Antibodies

One aspect of the invention pertains to isolated GAVE10 proteins and biologically active portions thereof, as well as polypeptide fragments suitable for use as immunogens to raise anti-GAVE10 antibodies. In one embodiment, native GAVE10 proteins can be isolated from cells or tissue sources by an appropriate purification scheme using standard protein purification techniques. In another embodiment, GAVE10 proteins are produced by recombinant DNA techniques. Alternative to recombinant expression, a GAVE10 protein or polypeptide can be synthesized chemically using standard peptide synthesis techniques.

An "isolated" or "purified" protein or biologically active portion thereof is substantially free of cellular material or other contaminating proteins from the cell or tissue source from that the GAVE10 protein is derived or substantially free of chemical precursors or other chemicals when chemically synthesized. The phrase, "substantially free of cellular material" includes preparations of GAVE10 protein in which the protein is separated from cellular components of the cells from which the protein is isolated or recombinantly produced. Thus, GAVE10 protein that is substantially free of cellular material includes preparations of GAVE10 protein having less than about 30%, 20%, 10% or 5% or less (by dry weight) of non-GAVE10 protein (also referred to herein as a "contaminating protein"). When the GAVE10 protein or biologically active portion thereof is produced recombinantly, it also is preferably substantially free of culture medium, i.e., culture medium represents less than about 20%, 10% or 5% or less of the volume of the protein preparation. When GAVE10 protein is produced by chemical synthesis, it is preferably substantially free of chemical precursors or other chemicals, i.e., it is separated from chemical precursors or other chemicals that are involved in the synthesis of the protein. Accordingly such preparations of GAVE10 protein have less than about 30%, 20%, 10% or 5% or less (by dry weight) of chemical precursors or non-GAVE10 chemicals.

Biologically active portions of a GAVE10 protein include peptides comprising amino acid sequences sufficiently identical to or derived from the amino acid sequence of the GAVE10 protein (e.g., the amino acid sequence shown in SEQ ID NO:2), that include fewer amino acids than the full length GAVE10 protein and exhibit at least one activity of a GAVE10 protein. Typically, biologically active portions comprise a domain or motif with at least one activity of a GAVE10 protein. A biologically active portion of a GAVE10 protein can be a polypeptide that is, for example, 10, 25, 50, 100 or more amino acids in length. Preferred biologically active polypeptides include one or more identified GAVE10 structural domains, e.g., the third intracellular loop domain (e.g., SEQ ID NO:2).

Moreover, other biologically active portions, in that other regions of the protein are deleted, can be prepared by recombinant techniques and evaluated for one or more of the functional activities of a native GAVE10 protein.

Preferred GAVE10 protein has the amino acid sequence shown of SEQ ID NO:2. Other useful GAVE10 proteins are substantially identical to SEQ ID NO:2 and retain a functional activity of the protein of SEQ ID NO:2 yet differ in amino acid sequence due to natural allelic variation or mutagenesis. For example, such GAVE10 proteins and polypeptides possess at least one biological activity described herein.

Accordingly, a useful GAVE10 protein is a protein that includes an amino acid sequence at least about 45%, preferably 55%, 65%, 75%, 85%, 95%, 99% or 100% identical to the amino acid sequence of SEQ ID NO:2 and retains a functional activity of a GAVE10 protein of SEQ ID NO:2. In other instances, the GAVE10 protein is a protein having an amino acid sequence 55%, 65%, 75%, 85%, 95%, 99% or 100% identical to the GAVE10 third intracellular loop domain (SEQ ID NO:2). In a preferred embodiment, the GAVE10 protein retains a functional activity of the GAVE10 protein of SEQ ID NO:2.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions then are compared. When a position in the first sequence is occupied by the same amino acid residue or nucleotide as the corresponding position in the second sequence, then the molecules are considered identical at that position. The percent identity between the two sequences is a function of the number of identical positions shared by the sequences (i.e., percent identity=number of identical positions/total number of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin et al., Proc Natl Acad Sci USA (1990) 87:2264, modified as in Karlin et al., Proc Natl Acad Sci USA (1993) 90:5873-5877. Such an algorithm is incorporated into the NBLAST and XBLAST programs of Altschul et al., J Mol Bio (1990) 215:403. BLAST nucleotide searches can be performed with the NBLAST program, for example, score=100, wordlength=12, to obtain nucleotide sequences homologous to GAVE10 nucleic acid molecules of the invention. BLAST protein searches can be performed with the XBLAST program, score=50, wordlength=3 to obtain amino acid sequences homologous to GAVE10 protein molecules of the invention. To obtain gapped alignments for comparison purposes, Gapped BLAST can be utilized as described in Altschul et al., Nucleic Acids Res (1997) 25:3389. Alternatively, PSI-Blast can be used to perform an iterated search that detects distant relationships between molecules. Altschul et al. (1997) supra. When utilizing BLAST, Gapped BLAST and PSI-Blast programs, the default parameters of the respective programs (e.g., XBLAST and NBLAST) can be used, see http://www.ncbi.nlm.nih.gov.

Another preferred, non-limiting example of a mathematical algorithm utilized for the comparison of sequences is the algorithm of Myers et al., CABIOS (1988) 4:11-17. Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used.

The percent identity between two sequences can be determined using techniques similar to those described above, with or without allowing gaps. In calculating percent identity, only exact matches are counted.

The invention also provides GAVE10 chimeric or fusion proteins. As used herein, a GAVE10 "chimeric protein" or "fusion protein" comprises a GAVE10 polypeptide operably linked to a non-GAVE10 polypeptide. A "GAVE10 polypeptide" refers to a polypeptide having an amino acid sequence corresponding to GAVE10. A "non-GAVE10 polypeptide" refers to a polypeptide having an amino acid sequence corresponding to a protein that is not substantially identical to the GAVE10 protein, e.g., a protein that is different from the GAVE10 protein and is derived from the same or a different organism. Within a GAVE10 fusion protein, the GAVE10 polypeptide can correspond to all or a portion of a GAVE10 protein, preferably at least one biologically active portion of a GAVE10 protein. Within the fusion protein, the term "operably linked" is intended to indicate that the GAVE10 polypeptide and the non-GAVE10 polypeptide are fused in-frame to each other. The non-GAVE10 polypeptide can be fused to the N-terminus or C-terminus of a GAVE10 polypeptide. One useful fusion protein is GST-GAVE10 in which the GAVE10 sequences are fused to the C-terminus of glutathione-S-transferase (GST). Such fusion proteins can facilitate the purification of recombinant GAVE10. In a preferred embodiment, the third intracellular loop (IC3 or IL3) of the instant invention (i.e., from about amino acid 202 to about 219 as set forth in SEQ ID NO:2) is fused with GST by PCR amplification of the IL3 and subcloning the product into a vector, such as, pGEX-2T. The resulting construct can be introduced into a host cell (e.g., E. coli) and expression from said construct can be induced by an appropriate small molecule (e.g., isopropyl-1-thio-β-D-galactopyranoside) and subsequently purified (see, e.g., Lee et al., J Biol Chem (1996) 271(19):11272-11279).

In certain host cells (e.g., mammalian host cells), expression and/or secretion of GAVE10 can be increased through use of a heterologous signal sequence. For example, the gp6 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is a GAVE10-immunoglobulin fusion protein in that all or part of GAVE10 is fused to sequences derived from a member of the immunoglobulin protein family. The GAVE10-immunoglobulin fusion proteins of the invention can be incorporated into pharmaceutical compositions and administered to a subject to inhibit an interaction between a GAVE10 ligand and a GAVE10 protein on the surface of a cell, thereby to suppress GAVE10-mediated signal transduction in vivo. The GAVE10-immunoglobulin fusion proteins can be used to affect the bioavailability of a GAVE10 cognate ligand. Inhibition of the GAVE10 ligand-GAVE10 interaction may be useful therapeutically, both for treating proliferative and differentiative disorders and for modulating (e.g. promoting or inhibiting) cell survival. Moreover, the GAVE10-immunoglobulin fusion proteins of the invention can be used as immunogens to produce anti-GAVE10 antibodies in a subject, to purify GAVE10 ligands and in screening assays to identify molecules that inhibit the interaction of GAVE10 with a GAVE10 ligand.

Preferably, a GAVE10 chimeric or fusion protein of the invention is produced by standard recombinant DNA techniques. For example, DNA fragments coding for the different polypeptide sequences are ligated together in-frame in accordance with conventional techniques, for example, by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that subsequently can be annealed and reamplified to generate a chimeric gene sequence (see e.g., Ausubel et al., supra). Moreover, many expression vectors are commercially available that already encode a fusion moiety (e.g., a GST polypeptide). A GAVE10-encoding nucleic acid can be cloned into such an expression vector such that the fusion moiety is linked in-frame to the GAVE10 protein.

The instant invention also pertains to variants of the GAVE10 proteins (i.e., proteins having a sequence that differs from that of the GAVE10 amino acid sequence). Such variants can function as either GAVE10 agonists (mimetics) or as GAVE10 antagonists. Variants of the GAVE10 protein can be generated by mutagenesis, e.g., discrete point mutation or truncation of the GAVE10 protein. An agonist of the GAVE10 protein can retain substantially the same or a subset, of the biological activities of the naturally occurring GAVE10 protein. An antagonist of the GAVE10 protein can inhibit one or more of the activities of the naturally occurring form of the GAVE10 protein by, for example, competitively binding to a downstream or upstream member of a cellular signaling cascade that includes the GAVE10 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the GAVE10 proteins.

Variants of the GAVE10 protein that function as either GAVE10 agonists (mimetics) or as GAVE10 antagonists can be identified by screening combinatorial libraries of mutants, e.g., truncation mutants, of the GAVE10 protein for GAVE10 agonist or antagonist activity. In one embodiment, a variegated library of GAVE10 variants is generated by combinatorial mutagenesis at the nucleic acid level and is encoded by a variegated gene library. A variegated library of GAVE10 variants can be produced by, for example, enzymatically ligating a mixture of synthetic oligonucleotides into gene sequences such that a degenerate set of potential GAVE10 sequences is expressed as individual polypeptides or alternatively, as a set of larger fusion proteins (e.g., for phage display) containing the set of GAVE10 sequences therein. There are a variety of methods that can be used to produce libraries of potential GAVE10 variants from a degenerate oligonucleotide sequence. Chemical synthesis of a degenerate gene sequence can be performed in an automated DNA synthesizer and the synthetic gene then ligated into an appropriate expression vector. Use of a degenerate set of genes allows for the provision, in one mixture, of all of the sequences encoding the desired set of potential GAVE10 sequences. Methods for synthesizing degenerate oligonucleotides are known in the art (see, e.g., Narang, Tetrahedron (1983) 39:3; Itakura et al., Ann Rev Biochem (1984) 53:323; Itakura et al., Science (1984) 198:1056; Ike et al., Nucleic Acid Res (1983) 11:477).

In addition, libraries of fragments of the GAVE10 protein coding sequence can be used to generate a variegated population of GAVE10 fragments for screening and subsequent selection of variants of a GAVE10 protein. In one embodiment, a library of coding sequence fragments can be generated by treating a double-stranded PCR fragment of a GAVE10 coding sequence with a nuclease under conditions wherein nicking occurs only about once per molecule, denaturing the double-stranded DNA, renaturing the DNA to form double-stranded DNA that can include sense/antisense pairs from different nicked products, removing single-stranded portions from reformed duplexes by treatment with SI nuclease and ligating the resulting fragment library into an expression vector. By that method, an expression library can be derived that encodes N-terminal and internal fragments of various sizes of the GAVE10 protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of GAVE10 proteins. The most widely used techniques, that are amenable to high throughput analysis, for screening large gene libraries typically include cloning the gene library into replicable expression vectors, transforming appropriate cells with the resulting library of vectors and expressing the combinatorial genes under conditions in that detection of a desired activity facilitates isolation of the vector encoding the gene whose product was detected. Recursive ensemble mutagenesis (REM), a technique that enhances the frequency of functional mutants in the libraries, can be used in combination with the screening assays to identify GAVE10 variants (Arkin et al., Proc Natl Acad Sci USA (1992) 89:7811-7815; Delgrave et al., Protein Engineering (1993) 6(3):327-331).

An isolated GAVE10 protein or a portion or fragment thereof, can be used as an immunogen to generate antibodies that bind GAVE10 using standard techniques for polyclonal and monoclonal antibody preparation. The full-length GAVE10 protein can be used or, alternatively, the invention provides antigenic peptide fragments of GAVE10 for use as immunogens. The antigenic peptide of GAVE10 comprises at least 8 (preferably 10, 15, 20, 30 or more) amino acid residues of the amino acid sequence shown in SEQ ID NO:2 and encompasses an epitope of GAVE10 such that an antibody raised against the peptide forms a specific immune complex with GAVE10.

In a related aspect, epitopes encompassed by the antigenic peptide are regions of GAVE10 that are located on the surface of the protein, e.g., hydrophilic regions. A hydrophobicity analysis of the human GAVE10 protein sequence indicates that the regions between about amino acids 1 and about 14, between about amino acids 72 and about 83, between about amino acids 145 and about 158 and between about amino acids 251 and about 258 of SEQ ID NO:2 are particularly hydrophilic and, therefore, are likely to encode surface residues useful for targeting antibody production.

A GAVE10 immunogen typically is used to prepare antibodies by immunizing a suitable subject, (e.g., rabbit, goat, mouse or other mammal) with the immunogen. An appropriate immunogenic preparation can contain, for example, recombinantly expressed GAVE10 protein or a chemically synthesized GAVE10 polypeptide. The preparation further can include an adjuvant, such as Freund's complete or incomplete adjuvant or similar immunostimulatory agent. Immunization of a suitable subject with an immunogenic GAVE10 preparation induces a polyclonal anti-GAVE10 antibody response.

Accordingly, another aspect of the invention pertains to anti-GAVE10 antibodies. The term "antibody" as used herein refers to immunoglobulin molecules and immunologically active portions of immunoglobulin molecules, i.e., molecules that contain an antigen-binding site that specifically binds an antigen, such as GAVE10. A molecule that specifically binds to GAVE10 is a molecule that binds GAVE10, but does not substantially bind other molecules in a sample, e.g., a biological sample, that naturally contains GAVE10. Examples of immunologically active portions of immunoglobulin molecules include $F_{(ab)}$ and $F_{(ab')2}$ fragments that can be generated by treating the antibody with an enzyme such as pepsin. The invention provides polyclonal and monoclonal antibodies that bind GAVE10. The term "monoclonal antibody" or "monoclonal antibody composition", as used herein, refers to a population of antibody molecules that contain only one species of an antigen-binding site capable of immunoreacting with a particular epitope of GAVE10. A monoclonal antibody composition thus typically displays a single binding affinity for a particular GAVE10 protein epitope.

Polyclonal anti-GAVE10 antibodies can be prepared as described above by immunizing a suitable subject with a GAVE10 immunogen. The anti-GAVE10 antibody titer in the immunized subject can be monitored over time by standard techniques, such as with an enzyme-linked immunosorbent assay (ELISA) using immobilized GAVE10. If desired, the antibody molecules directed against GAVE10 can be isolated from the mammal (e.g., from the blood) and further purified by well-known techniques, such as protein A chromatography, to obtain the IgG fraction. At an appropriate time after immunization, e.g., when the anti-GAVE10 antibody titers are highest, antibody-producing cells can be obtained from the subject and used to prepare monoclonal antibodies by standard techniques, such as the hybridoma technique originally described by Kohler et al., Nature (1975) 256:495-497, the human B cell hybridoma technique (Kohler et al., Immunol Today (1983) 4:72), the EBV hybridoma technique (Cole et al., Monoclonal Antibodies and Cancer Therapy, (1985), Alan R. Liss, Inc., pp. 77-96) or trioma techniques. The technology for producing hybridomas is well known (see generally Current Protocols in Immunology (1994) Coligan et al., eds., John Wiley & Sons, Inc., New York, N.Y.). Briefly, an immortal cell line (typically a myeloma) is fused to lymphocytes (typically splenocytes) from a mammal immunized with a GAVE10 immunogen as described above and the culture supernatants of the resulting hybridoma cells are screened to identify a hybridoma producing a monoclonal antibody that binds GAVE10.

Any of the many well known protocols used for fusing lymphocytes and immortalized cell lines can be applied for the purpose of generating an anti-GAVE10 monoclonal antibody (see, e.g., Current Protocols in Immunology, supra; Galfre et al., Nature (1977) 266:550-552; Kenneth, in Monoclonal Antibodies: A New Dimension In Biological Analyses, Plenum Publishing Corp., New York, N.Y. (1980); and Lerner, Yale J Biol Med (1981) 54:387-402). Moreover, the ordinarily skilled worker will appreciate that there are many variations of such methods that also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the instant invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Agl4 myeloma lines. The myeloma lines are available from ATCC. Typically, HAT-sensitive mouse myeloma cells are fused to mouse splenocytes using polyethylene glycol ("PEG"). Hybridoma cells resulting from the fusion then are selected using HAT medium that kills unfused and unproductively fused myeloma cells (unfused splenocytes die after several days because they are not transformed). Hybridoma cells producing a monoclonal antibody of the invention are detected by screening the hybridoma culture supernatants for antibodies that bind GAVE10, e.g., using a standard ELISA assay.

Alternative to preparing monoclonal antibody-secreting hybridomas, a monoclonal anti-GAVE10 antibody can be identified and isolated by screening a recombinant combinatorial immunoglobulin library (e.g., an antibody phage display library) with GAVE10 thereby to isolate immunoglobulin library members that bind GAVE10. Kits for generating and screening phage display libraries are commercially available (e.g., the Pharmacia Recombinant Phage Antibody System, Catalog No. 27-9400-01; and the Stratagene SurfZAP®Phage Display Kit, Catalog No. 240612).

Additionally, examples of methods and reagents particularly amenable for use in generating and screening antibody display libraries can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., Bio/Technology (1991) 9:1370-1372; Hay et al., Hum Antibody Hybridomas (1992) 3:81-85; Huse et al., Science (1989) 246:1275-1281; and Griffiths et al., EMBO J (1993) 25(12):725-734.

Additionally, recombinant anti-GAVE10 antibodies, such as chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in PCT Publication No. WO 87/02671; Europe Patent Application No. 184,187; Europe Patent Application No. 171,496; Europe Patent Application No. 173,494; PCT Publication No. WO 86/01533; U.S. Pat. No. 4,816,567; Europe Patent Application No. 125,023; Better et al., Science (1988) 240:1041-1043; Liu et al., Proc Natl Acad Sci USA (1987) 84:3439-3443; Lin et al., J Immunol (1987) 139:3521-3526; Sun et al., Proc Natl Acad Sci USA (1987) 84:214-218; Nishimura et al., Canc Res (1987) 47:999-1005; Wood et al., Nature (1985) 314:446-449; Shaw et al., J Natl Cancer Inst (1988) 80:1553-1559; Morrison, Science (1985) 229:1202-1207; Oi et al., Bio/Techniques (1986) 4:214; U.S. Pat. No. 5,225,539; Jones et al., Nature (1986) 321:552-525; Verhoeyan et al., Science (1988) 239: 1534; and Beidler et al., J Immunol (1988) 141:4053-4060.

Completely human antibodies are particularly desirable for therapeutic treatment of human patients. Such antibodies can be produced using transgenic mice that are incapable of expressing endogenous immunoglobulin heavy and light chains genes, but that can express human heavy and light chain genes. The transgenic mice are immunized in the normal fashion with a selected antigen, e.g., all or a portion of GAVE10. Monoclonal antibodies directed against the antigen can be obtained using conventional hybridoma technology. The human immunoglobulin transgenes harbored by the transgenic mice rearrange during B cell differentiation and subsequently undergo class switching and somatic mutation. Thus, using such an epitope, e.g., an antibody that inhibits GAVE10 activity is identified. The heavy chain and the light chain of the non-human antibody are cloned and used to create phage display $F_{ab}$ fragments. For example, the heavy chain gene can be cloned into a plasmid vector so that the heavy chain can be secreted from bacteria. The light chain gene can be cloned into a phage coat protein gene so that the light chain can be expressed on the surface of phage. A repertoire (random collection) of human light chains fused to phage is used to infect the bacteria that express the non-human heavy chain. The resulting progeny phage display hybrid antibodies (human light chain/non-human heavy chain). The selected antigen is used in a panning screen to select phage that bind the selected antigen. Several rounds of selection may be required to identify such phage.

Human light chain genes are isolated from the selected phage that bind the selected antigen. The selected human light chain genes then are used to guide the selection of human heavy chain genes as follows. The selected human light chain genes are inserted into vectors for expression by bacteria. Bacteria expressing the selected human light chains are infected with a repertoire of human heavy chains fused to phage. The resulting progeny phage display human antibodies (human light chain/human heavy chain).

Next, the selected antigen is used in a panning screen to select phage that bind the selected antigen. The selected phage display a completely human antibody that recognizes the same epitope recognized by the original selected, non-human monoclonal antibody. The genes encoding both the heavy and light chains are isolated and can be manipulated further for production of human antibody. The technology is described by Jespers et al. (Bio/Technology (1994) 12:899-903).

An anti-GAVE10 antibody (e.g., monoclonal antibody) can be used to isolate GAVE10 by standard techniques, such as affinity chromatography or immunoprecipitation. An anti-GAVE10 antibody can facilitate the purification of natural GAVE10 from cells and of recombinantly produced GAVE10 expressed in host cells. Moreover, an anti-GAVE10 antibody can be used to detect GAVE10 protein (e.g., in a cellular lysate or cell supernatant) to evaluate the abundance and pattern of expression of the GAVE10 protein. Anti-GAVE10 antibodies can be used diagnostically to monitor protein levels in tissue as part of a clinical testing procedure, for example, to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials and radioactive materials. Examples of suitable enzymes include horseradish peroxidase, alkaline phosphatase, galactosidase or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrins. An example of a luminescent material is luminol. Examples of bioluminescent materials include luciferase, luciferin and aequorin. Examples of suitable radioactive materials include $^{125}I$, $^{131}I$, $^{35}S$ or $^{3}H$.

Recombinant Expression Vectors and Host Cells

Another aspect of the invention pertains to vectors, preferably expression vectors, containing a nucleic acid encoding GAVE10 (or a portion thereof). As used herein, the term "vector" refers to a nucleic acid molecule capable of transporting another nucleic acid linked thereto. One type of vector is a "plasmid" that refers to a circular double-stranded DNA loop into that additional DNA segments can be ligated. Another type of vector is a viral vector, wherein additional DNA segments can be ligated into a viral genome. Certain vectors are capable of autonomous replication in a host cell (e.g., bacterial vectors having a bacterial origin of replication and episomal mammalian vectors). Other vectors (e.g., non-episomal mammalian vectors) are integrated into the genome of a host cell on introduction into the host cell and thereby are replicated along with the host genome. Moreover, certain vectors, expression vectors, are capable of directing the expression of genes operably linked thereto. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), that serve equivalent functions.

The recombinant expression vectors of the invention comprise nucleic acid of the invention in a form suitable for expression of the nucleic acid in a host cell. That means the recombinant expression vectors include one or more regulatory sequences, selected on the basis of the host cells to be used for expression, that is operably linked to the nucleic acid to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology Vol. 185, Academic Press, San Diego, Calif. (1990). Regulatory sequences include those that direct constitutive expression of the nucleotide sequence in many types of host cells (e.g., tissue specific regulatory sequences). It will be appreciated by those skilled in the art that the design of the expression vector can depend on such factors as the choice of host cell to be transformed, the level of expression of protein desired etc. The expression vectors of the invention can be introduced into host cells to produce proteins or peptides encoded by nucleic acids as described herein (e.g., GAVE10 proteins, mutant forms of GAVE10, fusion proteins etc.).

The recombinant expression vectors of the invention can be designed for expression of GAVE10 in prokaryotic or eukaryotic cells, e.g., bacterial cells such as *E. coli,* insect cells (using baculovirus expression vectors), yeast cells or mammalian cells. Suitable host cells are discussed further in Goeddel, supra. Alternatively, the recombinant expression vector can be transcribed and translated in vitro, for example using phage regulatory elements and proteins, such as, a T7 promoter and/or a T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes and the cognate recognition sequences, include Factor Xa, thrombin and enterokinase. Typical fusion expression vectors include pGEX (Pharmacia Biotech Inc; Smith et al., Gene (1988) 67:31-40), pMAL (New England Biolabs, Beverly, Mass.) and pRITS (Pharmacia, Piscataway, N.J.), that fuse glutathione 5-transferase (GST), maltose E binding protein or protein A, respectively, to the target recombinant protein.

Examples of suitable inducible non-fusion *E. coli* expression vectors include pTrc (Amann et al., Gene (1988) 69:301-315) and pET 11d (Studier et al., Gene Expression Technology: Methods in Enzymology, Academic Press, San Diego, Calif. (1990) 185:60-89). Target gene expression from the pTrc vector relies on host RNA polymerase transcription from a hybrid trp-lac fusion promoter.

One strategy to maximize recombinant protein expression in *E. coli* is to express the protein in a host with impaired capacity to cleave proteolytically the recombinant protein (Gottesman, Gene Expression Technology: Methods in Enzymology, Academic Press, San Diego, Calif. (1990) 185:119-128). Another strategy is to alter the nucleic acid sequence of the nucleic acid to be inserted into an expression vector so that the individual codons for each amino acid are those preferentially utilized in *E. coli* (Wada et al., Nucleic Acids Res (1992) 20:2111-2118). Such alteration of nucleic acid sequences of the invention can be carried out by standard DNA synthesis techniques.

In another embodiment, the GAVE10 expression vector is a yeast expression vector. Examples of vectors for expression in yeast such as *S. cerevisiae* include pYepSec1 (Baldari et al., EMBO J (1987) 6:229-234), pMFa (Kurjan et al., Cell (1982) 30:933-943), pJRY88 (Schultz et al., Gene (1987) 54:113-123), pYES2 (Invitrogen Corporation, San Diego, Calif.) and pPicZ (Invitrogen Corp, San Diego, Calif.).

Alternatively, GAVE10 can be expressed in insect cells using baculovirus expression vectors. Baculovirus vectors available for expression of proteins in cultured insect cells (e.g., Sf9 cells) include the pAc series (Smith et al., Mol Cell Biol (1983) 3:2156-2165) and the pVL series (Lucklow et al., Virology (1989) 170:31-39).

In yet another embodiment, a nucleic acid of the invention is expressed in mammalian cells using a mammalian expression vector. Examples of mammalian expression vectors include pCDM8 (Seed, Nature (1987) 329:840) and pMT2PC (Kaufman et al., EMBO J (1987) 6:187-195). When used in mammalian cells, the control functions of the expression vector often are provided by viral regulatory elements. For example, commonly used promoters are derived from polyoma, adenovirus 2, cytomegalovirus and simian virus 40. For other suitable expression systems for both prokaryotic and eukaryotic cells, see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., Genes Dev (1987) 1:268-277), lymphoid-specific promoters (Calame et al., Adv Immunol (1988) 43:235-275), in particular, promoters of T cell receptors (Winoto et al., EMBO J (1989) 8:729-733) and immunoglobulins (Banerji et al., Cell (1983) 33:729-740; Queen et al., Cell (1983) 33:741-748), neuron-specific promoters (e.g., the neurofilament promoter; Byrne et al., Proc Natl Acad Sci USA (1989) 86:5473-5477), pancreas-specific promoters (Edlund et al., Science (1985) 230:912-916) and mammary gland-specific promoters (e.g., milk whey promoter; U.S. Pat. No. 4,873,316 and Europe Application No. 264,166). Developmentally-regulated promoters also are encompassed, for example the murine hox promoters (Kessel et al., Science (1990) 249:374-379) and the α-fetoprotein promoter (Campes et al., Genes Dev (1989) 3:537-546).

The invention further provides a recombinant expression vector comprising a DNA molecule of the invention cloned into an expression vector in an antisense orientation. That is, the DNA molecule is operably linked to a regulatory sequence in a manner that allows for expression (by transcription of the DNA molecule) of an RNA molecule that is antisense to GAVE10 mRNA. Regulatory sequences operably linked to a nucleic acid cloned in the antisense orientation can be chosen that direct the continuous expression of the antisense RNA molecule in a variety of cell types. For example, viral promoters and/or enhancers or regulatory sequences can be chosen that direct constitutive, tissue-specific or cell type-specific expression of antisense RNA. The antisense expression vector can be in the form of a recombinant plasmid, phagemid or attenuated virus in that antisense nucleic acids are produced under the control of a high efficiency regulatory region, the activity of that can be determined by the cell type into that the vector is introduced. For a discussion of the regulation of gene expression using antisense genes, see Weintraub et al. (Reviews-Trends in Genetics, Vol. 1(1)1986).

Another aspect of the invention pertains to host cells into that a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but still are included within the scope of the term as used herein.

A host cell can be any prokaryotic or eukaryotic cell. For example, GAVE10 protein can be expressed in bacterial cells such as *E. coli,* insect cells, yeast or mammalian cells (such as Chinese hamster ovary cells (CHO), 293 cells or COS cells). Other suitable host cells are known to those skilled in the art. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, transduction, DEAE-dextran-mediated transfection, lipofection or electroporation.

For stable transfection of mammalian cells, it is known that, depending on the expression vector and transfection technique used, only a small fraction of cells may integrate the foreign DNA into the genome. To identify and to select the integrants, a gene that encodes a selectable marker (e.g., for resistance to antibiotics) generally is introduced into the host cells along with the gene of interest. Preferred selectable markers include those that confer resistance to drugs, such as G418, hygromycin and methotrexate. Nucleic acid encoding a selectable marker can be introduced into a host cell on the same vector as that encoding GAVE10 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) GAVE10 protein. Accordingly, the invention further provides methods for producing GAVE10 protein using the host cells of the invention. In one embodiment, the method comprises culturing the host cell of invention (into that a recombinant expression vector encoding GAVE10 has been introduced) in a suitable medium such that GAVE10 protein is produced. In another embodiment, the method further comprises isolating GAVE10 from the medium or the host cell.

In another embodiment, GAVE10 comprises an inducible expression system for the recombinant expression of other proteins subcloned in modified expression vectors. For example, host cells comprising a mutated G protein (e.g., yeast cells, Y2 adrenocortical cells and cyc⁻ S49, see U.S. Pat. Nos. 6,168,927 B1, 5,739,029 and 5,482,835; Mitchell et al., Proc Natl Acad Sci USA (1992) 89(19):8933-37 and Katada et al., J Biol Chem (1984) 259(6):3586-95) are transduced with a first expression vector comprising a nucleic acid sequence encoding GAVE10, wherein said GAVE10 is functionally expressed in the host cells. Even though the expressed GAVE10 is constitutively active, the mutation does not allow for signal transduction; i.e., no activation of a G-protein directed downstream cascade occurs (e.g., no adenylyl cyclase activation). Subsequently, a second expression vector is used to transduce the GAVE10-comprising host cells. The second vector comprises a structural gene that complements the G protein mutation of the host cell (i.e., functional mammalian or yeast $G_s$, $G_i$, $G_o$, or $G_q$, e.g., see PCT Publication No. WO 97/48820; U.S. Pat. Nos. 6,168,927 B1, 5,739,029 and 5,482,835) in addition to the gene of interest to be expressed by the inducible system. The complementary structural gene of the second vector is inducible; i.e., under the control of an exogenously added component (e.g., tetracycline, IPTG, small molecules etc., see Sambrook et al. supra) that activates a promoter which is operably linked to said complementary structural gene. On addition of the inducer, the protein encoded by said complementary structural gene is functionally expressed such that the constitutively active GAVE10 now will form a complex that leads to appropriate downstream pathway activation (e.g., second messenger formation). The gene of interest comprising the second vector possesses an operably linked promoter that is activated by the appropriate second messenger (e.g., CREB, AP1 elements). Thus, as second messenger accumulates, the promoter upstream from the gene of interest is activated to express the product of said gene. When the inducer is absent, expression of the gene of interest is switched off.

In a preferred embodiment, the host cells for the inducible expression system include, but are not limited to, S49 (cyc$^-$) cells. While cell lines are contemplated that comprise G-protein mutations, suitable mutants may be artificially produced/constructed (see U.S. Pat. Nos. 6,168,927 B1, 5,739,029 and 5,482,835 for yeast cells).

In a related aspect, the cells are transfected with a vector operably linked to a cDNA comprising a sequence encoding a protein as set forth in SEQ ID NO:2. The first and second vectors comprising said system are contemplated to include, but are not limited to, pCDM8 (Seed, Nature (1987) 329:840) and pMT2PC (Kaufman et al., EMBO J (1987) 6:187-195), pYepSec1 (Baldari et al., EMBO J (1987) 6:229-234), pMFa (Kurjan et al., Cell (1982) 30:933-943), pJRY88 (Schultz et al., Gene (1987) 54:113-123), pYES2 (Invitrogen Corporation, San Diego, Calif.) and pPicZ (Invitrogen Corp, San Diego, Calif.).

In a related aspect, the host cells may be transfected by such suitable means wherein transfection results in the expression of a functional GAVE10 protein (e.g., Sambrook et al., supra, and Kriegler, Gene Transfer and Expression: A Laboratory Manual, Stockton Press, New York, N.Y., 1990). Such "functional proteins" include, but are not limited to, proteins that once expressed, form complexes with G-proteins, where said G-proteins regulate second messenger formation.

In a further related aspect, the promoters contemplated for the genes of interest include, but are not limited to, those derived from polyoma, Adenovirus 2, cytomegalovirus and Simian Virus 40. Other expression construct combination are suitable for the inducible system (see Sambrook et al., supra and Kriegler, supra).

The host cells of the invention also can be used to produce nonhuman transgenic animals. For example, in one embodiment, a host cell of the invention is a fertilized oocyte or an embryonic stem cell into that GAVE10-coding sequences have been introduced. Such host cells then can be used to create non-human transgenic animals in that exogenous GAVE10 sequences have been introduced into the genome or homologous recombinant animals in that endogenous GAVE10 sequences have been altered. Such animals are useful for studying the function and/or activity of GAVE10 and for identifying and/or evaluating modulators of GAVE10 activity. As used herein, a "transgenic animal" is a non-human animal, preferably a mammal, more preferably a rodent such as a rat or mouse, in that one or more of the cells of the animal includes a transgene. Other examples of transgenic animals include non-human primates, sheep, dogs, cows, goats, chickens, amphibians etc.

A transgene is exogenous DNA that is integrated into the genome of a cell from which a transgenic animal develops and that remains in the genome of the mature animal. The transgene directs the expression of an encoded gene product in one or more cell types or tissues of the transgenic animal. As used herein, a "homologous recombinant animal" is a non-human animal, preferably a mammal, more preferably a mouse, in which an endogenous GAVE10 gene has been altered by homologous recombination. That is accomplished between the endogenous gene and an exogenous DNA molecule introduced into a cell of the animal, e.g., an embryonic cell of the animal, prior to development of the animal.

A transgenic animal of the invention can be created by introducing GAVE10-encoding nucleic acid into the male pronuclei of a fertilized oocyte, e.g., by microinjection or retroviral infection and allowing the oocyte to develop in a pseudopregnant female foster animal. The GAVE10 cDNA sequence e.g., that of (SEQ ID NO:1), can be introduced as a transgene into the genome of a non-human animal. Alternatively, a nonhuman homologue of the human GAVE10 gene, such as a mouse GAVE10 gene, can be isolated based on hybridization to the human GAVE10 cDNA and used as a transgene. Intronic sequences and polyadenylation signals also can be included in the transgene to increase the efficiency of expression of the transgene. A tissue-specific regulatory sequence(s) can be operably linked to the GAVE10 transgene to direct expression of GAVE10 protein in particular cells. Methods for generating transgenic animals via embryo manipulation and microinjection, particularly animals such as mice, are conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals with a transgene in the genome and/or expression of GAVE10 mRNA in tissues or cells of the animals. A transgenic founder animal then can be used to breed additional animals carrying the transgene. Moreover, transgenic animals carrying a transgene encoding GAVE10 can be bred further to other transgenic animals carrying other transgenes.

To create a homologous recombinant animal, a vector is prepared that contains at least a portion of a GAVE10 gene (e.g., a human or a non-human homolog of the GAVE10 gene, e.g., a murine GAVE10 gene) into which a deletion, addition or substitution has been introduced thereby to alter, e.g., functionally disrupt, the GAVE10 gene. In a preferred embodiment, the vector is designed such that, on homologous recombination, the endogenous GAVE10 gene is disrupted functionally (i.e., no longer encodes a functional protein; also referred to as a "knock out" vector).

Alternatively, the vector can be designed such that, on homologous recombination, the endogenous GAVE10 gene is mutated or otherwise altered but still encodes functional protein (e.g., the upstream regulatory region can be altered thereby to alter the expression of the endogenous GAVE10 protein).

In the homologous recombination vector, the altered portion of the GAVE10 gene is flanked at the 5' and 3' ends by additional nucleic acid of the GAVE10 gene to allow for homologous recombination to occur between the exogenous GAVE10 gene carried by the vector and an endogenous GAVE10 gene in an embryonic stem cell. The additional flanking GAVE10 nucleic acid is of sufficient length for successful homologous recombination with the endogenous gene. Typically, several kilobases of flanking DNA (both at the 5' and 3' ends) are included in the vector (see, e.g., Thomas et al., Cell (1987) 51:503 for a description of homologous recombination vectors).

The vector is introduced into an embryonic stem cell line (e.g., by electroporation) and cells in that the introduced GAVE10 gene has homologously recombined with the endogenous GAVE10 gene are selected (see, e.g., Li et al., Cell (1992) 69:915). The selected cells then are injected into a blastocyst of an animal (e.g., a mouse) to form aggregation chimeras (see, e.g., Bradley in Teratocarcinomas and Embryonic Stem Cells: A Practical Approach, Robertson, ed., IRL, Oxford, (1987) pp. 113-152). A chimeric embryo then can be implanted into a suitable pseudopregnant female foster animal and the embryo brought to term. Progeny harboring the homologously recombined DNA in the germ cells can be used to breed animals in that all cells of the animal contain the homologously recombined DNA by germline transmission of the transgene.

Methods for constructing homologous recombination vectors and homologous recombinant animals are described further in Bradley, Current Opinion in Bio/Technology (1991) 2:823-829 and in PCT Publication Nos. WO 90/11354, WO 91/01140, WO 92/0968 and WO 93/04169.

In another embodiment, transgenic non-human animals can be produced that contain selected systems to allow for regulated expression of the transgene. One example of such a system is the cre/loxP recombinase system of bacteriophage P1. For a description of the cre/loxP recombinase system, see, e.g., Lakso et al., Proc Natl Acad Sci USA (1992) 89:6232-6236. Another example of a recombinase system is the FLP recombinase system of S. cerevisiae (O'Gorrnan et al., Science (1991) 251:1351-1355). If a cre/loxP recombinase system is used to regulate expression of the transgene, animals containing transgenes encoding both the cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein also can be produced according to the methods described in Wilmut et al., Nature (1997) 385:810-813 and PCT Publication Nos. WO 97/07668 and WO 97/07669. In brief, a cell, e.g., a somatic cell, from the transgenic animal can be isolated and induced to exit the growth cycle and enter $G_0$ phase. The quiescent cell then can be fused, e.g., through the use of electrical pulses, to an enucleated oocyte from an animal of the same species from that the quiescent cell is isolated. The reconstructed oocyte then is cultured such that it develops to morula or blastocyte and then transferred to pseudopregnant female foster animal. The offspring borne of the female foster animal will be a clone of the animal from that the cell, e.g., the somatic cell, is isolated.

Pharmaceutical Compositions

The GAVE10 nucleic acid molecules, GAVE10 proteins and anti-GAVE10 antibodies (also referred to herein as "active compounds") of the invention can be incorporated into pharmaceutical compositions suitable for administration. Such compositions typically comprise the nucleic acid molecule, protein or antibody, and a pharmaceutically acceptable carrier. As used herein, the language "pharmaceutically acceptable carrier" is intended to include any and all solvents, dispersion media, coatings, antibacterial and antifungal agents, isotonic and absorption delaying agents and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds also can be incorporated into the compositions.

A pharmaceutical composition of the invention is formulated to be compatible with the intended route of administration. Examples of routes of administration include parenteral, e.g., intravenous, intradermal, subcutaneous, oral (e.g., inhalation), transdermal (topical), transmucosal and rectal administration. Solutions or suspensions used for parenteral, intradermal or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose. pH can be adjusted with acids or bases, such as HCl or NaOH. The parenteral preparation can be enclosed in ampoules, disposable syringes or multiple dose vials made of glass or plastic.

Pharmaceutical compositions suitable for injectable use include sterile aqueous solutions (water miscible) or dispersions and sterile powders for the extemporaneous preparation of sterile injectable solutions or dispersions. For intravenous administration, suitable carriers include physiological saline, bacteriostatic water, Cremophor EL® (BASF; Parsippany, N.J.) or phosphate buffered saline (PBS). In all cases, the composition must be sterile and should be fluid to the extent that easy syringability exists. The composition must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyetheylene glycol and the like) and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols such as mannitol, sorbitol or sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound (e.g., a GAVE10 protein or anti-GAVE10 antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of the active ingredient plus any additional desired ingredient from a previously sterile-filtered solution thereof.

Oral compositions generally include an inert diluent or an edible carrier. The compositions can be enclosed in gelatin capsules or compressed into tablets. For the purpose of oral therapeutic administration, the active compound can be incorporated with excipients and used in the form of tablets, troches or capsules. Oral compositions also can be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate or orange flavoring. For administration by inhalation, the compounds are delivered in the form of an aerosol spray from a pressurized container or dispenser that contains a suitable propellant, e.g., a gas such as carbon dioxide or a nebulizer.

Systemic administration also can be by transmucosal or transdermal means. For transmucosal or transdermal administration, penetrants appropriate to the barrier to be permeated are used in the formulation. Such penetrants generally are known in the art and include, for example, for transmucosal administration, detergents, bile salts and fusidic acid derivatives. Transmucosal administration can be accomplished through the use of nasal sprays or suppositories. For transdermal administration, the active compounds are formulated into ointments, salves, gels or creams as generally known in the art.

The compounds also can be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials also can be obtained commercially from Alza Corporation and Nova Pharmaceuticals, Inc. Liposomal suspensions (including liposomes targeted to infected cells with monoclonal antibodies) also can be used as pharmaceutically acceptable carriers. Those can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. Depending on the type and severity of the disease, about 1 µg/kg to 15 mg/kg (e.g., 0.1 to 20 mg/kg) of antibody is an initial candidate dosage for administration to the patient, whether, for example, by one or more separate administrations or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of the therapy is monitored easily by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al., Proc Natl Acad Sci USA (1994) 91:3054-3057). The pharmaceutical preparation of the gene therapy vector can include the gene therapy vector in an acceptable diluent or can comprise a slow release matrix in that the gene delivery vehicle is imbedded. Alternatively, where the complete gene delivery vector can be produced intact from recombinant cells, e.g. retroviral vectors, the pharmaceutical preparation can include one or more cells that produce the gene delivery system.

The pharmaceutical compositions can be included in a container, pack or dispenser together with instructions for administration.

Uses and Methods of the Invention

The nucleic acid molecules, proteins, protein homologues and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials and pharmacogenomics); and d) methods of treatment (e.g., therapeutic and prophylactic). A GAVE10 protein interacts with other cellular proteins and thus can be used for (i) regulation of cellular proliferation; (ii) regulation of cellular differentiation; and (iii) regulation of cell survival. The isolated nucleic acid molecules of the invention can be used to express GAVE10 protein (e.g., via a recombinant expression vector in a host cell in gene therapy applications), to detect GAVE10 mRNA (e.g., in a biological sample) or to detect a genetic lesion in a GAVE10 gene and to modulate GAVE10 activity. In addition, the GAVE10 proteins can be used to screen drugs or compounds that modulate GAVE10 activity or expression as well as to treat disorders characterized by insufficient or excessive production of GAVE10 protein or by production of GAVE10 protein forms that have decreased or aberrant activity compared to GAVE10 wild type protein. In addition, the anti-GAVE10 antibodies of the invention can be used to detect and to isolate GAVE10 proteins and to modulate GAVE10 activity. The invention further pertains to novel agents identified by the above-described screening assays and uses thereof for treatments as described herein.

A. Screening Assays

Activation of G protein receptors in the presence of endogenous ligand allows for G protein receptor complex formation, thereupon leading to the binding of GTP to the G protein. The GTPase domain of the G protein slowly hydrolyzes the GTP to GDP resulting, under normal conditions, in receptor deactivation. However, constitutively activated receptors continue to hydrolyze GDP to GTP.

A non-hydrolyzable substrate of G protein, [$^{35}$S]GTPγS, can be used to monitor enhanced binding to membranes which express constitutively activated receptors. Traynor and Nahorski reported that [$^{35}$S]GTPγS can be used to monitor G protein coupling to membranes in the absence and presence of ligand (Traynor et al., Mol Pharmacol (1995) 47(4):848-54). A preferred use of such an assay system is for initial screening of candidate compounds since the system is generically applicable to all G protein-coupled receptors without regard to the particular G protein that binds to the receptor.

$G_{s20}$ stimulates the enzyme adenylyl cyclase, while $G_i$ and $G_o$ inhibit that enzyme. As is well known the art, adenylyl cyclase catalyzes the conversion of ATP to cAMP; thus, constitutively activated GPCRs that couple the $G_s$ protein are associated with increased cellular levels of cAMP. Alternatively, constitutively activated GCPRs that might couple the $G_i$ (or $G_o$) protein are associated with decreased cellular levels of cAMP. See "Indirect Mechanism of Synaptic Transmission", Chpt. 8, from Neuron to Brain ($3^{rd}$ Ed.), Nichols et al. eds., Sinauer Associates, Inc., 1992. Thus, assays that detect cAMP can be used to determine if a candidate compound is an inverse agonist to the receptor. A variety of approaches known in the art for measuring cAMP can be utilized. In one embodiment, anti-cAMP antibodies are used in an ELISA-based format. In another embodiment, a whole cell second messenger reporter system assay is contemplated (see PCT Publication No. WO 00/22131).

In a related aspect, cyclic AMP drives gene expression by promoting the binding of a cAMP-responsive DNA binding protein or transcription factor (CREB) which then binds to the promoter at specific sites called cAMP response elements and drives the expression of the gene. Thus, reporter systems can be constructed which have a promoter containing multiple cAMP response elements before the reporter gene, e.g., β-galactosidase or luciferase. Further, as a constitutively activated $G_s$-linked receptor causes the accumulation of cAMP, that then activates the gene and expression of the reporter protein. The reporter protein, such as β-galactosidase or luciferase, then can be detected using standard biochemical assays (PCT Publication No. WO 00/22131).

Other G proteins, such as $G_o$ and $G_q$, are associated with activation of the enzyme, phospholipase C, which in turn hydrolyzes the phospholipid, PIP2, releasing two intracellular messengers: diacylglycerol (DAG) and inositol 1,4,5-triphosphate (IP3). Increased accumulation of IP3 is associated with activation of $G_q$-associated receptors and $G_o$-associated receptors (PCT Publication No. WO 00/22131). Assays that detect IP3 accumulation can be used to determine if a candidate compound is an inverse agonist to a $G_q$-associated receptor or a $G_o$-associated receptor. $G_q$-associated receptors also can be examined using an AP1 reporter assays that measures whether $G_q$-dependent phospholipase C causes activation of genes containing AP1 elements. Thus, activated $G_q$-associated receptors will demonstrate an increase in the expression of such genes, whereby inverse agonists will demonstrate a decrease in such expression.

The invention provides a method (also referred to herein as a "screening assay") for identifying modulators, i.e., candidate or test compounds or agents (e.g., peptides, peptidomimetics, small molecules or other drugs) that bind to GAVE10 proteins or have a stimulatory or inhibitory effect on, for example, GAVE10 expression or GAVE10 activity.

In one embodiment, the invention provides assays for screening candidate or test compounds that bind to or modulate the activity of the membrane-bound form of a GAVE10 protein, polypeptide or biologically active portion thereof.

The test compounds of the instant invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, Anticancer Drug Des (1997) 12:145).

Examples of methods for the synthesis of molecular libraries can be found in the art, for example in: DeWitt et al., Proc Natl Acad Sci USA (1993) 90:6909; Erb et al., Proc Natl Acad Sci USA (1994) 91:11422; Zuckermann et al., J Med Chem (1994) 37:2678; Cho et al., Science (1993) 261:1303; Carrell et al., Angew Chem Int Ed Engl (1994) 33:2059; Carell et al., Angew Chem Int Ed Engl (1994) 33:2061; and Gallop et al., J Med Chem (1994) 37:1233.

Libraries of compounds may be presented in solution (e.g., Houghten Bio/Techniques (1992) 13:412-421) or on beads (Lam, Nature (1991) 354:82-84), chips (Fodor, Nature (1993) 364:555-556), bacteria (U.S. Pat. No. 5,223,409), spores (U.S. Pat. Nos. 5,571,698; 5,403,484; and 5,223,409), plasmids (Cull et al., Proc Natl Acad Sci USA (1992) 89:1865-1869) or phage (Scott et al., Science (1990) 249:386-390; Devlin, Science (1990) 249:404-406; Cwirla et al., Proc Natl Acad Sci USA (1990) 87:6378-6382; and Felici, J Mol Biol (1991) 222:301-310).

In one embodiment, an assay is a cell-based assay in which a cell that expresses a membrane-bound form of GAVE10 protein, or a biologically active portion thereof, on the cell surface is contacted with a test compound and the ability of the test compound to bind to a GAVE10 protein is determined. The cell, for example, can be a yeast cell or a cell of mammalian origin. Determining the ability of the test compound to bind to the GAVE10 protein can be accomplished, for example, by coupling the test compound with a radioisotope or enzymatic label such that binding of the test compound to the GAVE10 protein or biologically active portion thereof can be determined by detecting the labeled compound in a complex. For example, test compounds can be labeled with $^{125}$I, $^{35}$S, $^{14}$C or $^3$H, either directly or indirectly and the radioisotope detected by direct counting of radioemmission or by scintillation counting. Alternatively, test compounds can be labeled enzymatically with, for example, horseradish peroxidase, alkaline phosphatase or luciferase and the enzymatic label detected by determination of conversion of an appropriate substrate to product. In a preferred embodiment, the assay comprises contacting a cell that expresses a membrane-bound form of GAVE10 protein or a biologically active portion thereof, on the cell surface with a known compound that binds GAVE10 to form an assay mixture, contacting the assay mixture with a test compound and determining the ability of the test compound to interact with a GAVE10 protein, wherein determining the ability of the test compound to interact with a GAVE10 protein comprises determining the ability of the test compound to bind preferentially to GAVE10 or a biologically active portion thereof as compared to the known compound.

In another embodiment, an assay is a cell-based assay comprising contacting a cell expressing a membrane-bound form of GAVE10 protein or a biologically active portion thereof, on the cell surface with a test compound and determining the ability of the test compound to modulate (e.g., stimulate or inhibit) the activity of the GAVE10 protein or biologically active portion thereof. Determining the ability of the test compound to modulate the activity of GAVE10 or a biologically active portion thereof can be accomplished, for example, by determining the ability of the GAVE10 protein to bind to or to interact with a GAVE10 target molecule. As used herein, a "target molecule" is a molecule with that a GAVE10 protein binds or interacts in nature, for example, a molecule on the surface of a cell that expresses a GAVE10 protein, a molecule on the surface of a second cell, a molecule in the extracellular milieu, a molecule associated with the internal surface of a cell membrane or a cytoplasmic molecule. A GAVE10 target molecule can be a non-GAVE10 molecule or a GAVE10 protein or polypeptide of the instant invention. In one embodiment, a GAVE10 target molecule is a component of a signal transduction pathway that facilitates transduction of an extracellular signal (e.g., a signal generated by binding of a compound to a membrane-bound GAVE10 molecule) through the cell membrane and into the cell. The target, for example, can be a second intercellular protein that has catalytic activity or a protein that facilitates the association of downstream signaling molecules with GAVE10.

Determining the ability of the GAVE10 protein to bind to or to interact with a GAVE10 target molecule can be accomplished by one of the methods described above for determining direct binding. In a preferred embodiment, determining the ability of the GAVE10 protein to bind to or to interact with a GAVE10 target molecule can be accomplished by determining the activity of the target molecule. For example, the activity of the target molecule can be determined by detecting induction of a cellular second messenger of the target (e.g., intracellular $Ca^{2+}$, diacylglycerol, IP3 etc.), detecting catalytic/enzymatic activity of the target on an appropriate substrate, detecting the induction of a reporter gene (e.g., a GAVE10-responsive regulatory element operably linked to a nucleic acid encoding a detectable marker, e.g. luciferase) or detecting a cellular response, for example, cellular differentiation or cell proliferation.

In yet another embodiment, an assay of the instant invention is a cell-free assay comprising contacting a GAVE10 protein or biologically active portion thereof with a test compound and determining the ability of the test compound to bind to the GAVE10 protein or biologically active portion thereof. Binding of the test compound to the GAVE10 protein can be determined either directly or indirectly as described above. In a preferred embodiment, the assay includes contacting the GAVE10 protein or biologically active portion thereof with a known compound that binds GAVE10 to form an assay mixture, contacting the assay mixture with a test compound and determining the ability of the test compound to interact with a GAVE10 protein, wherein determining the ability of the test compound to interact with a GAVE10 protein comprises determining the ability of the test compound to preferentially bind to GAVE10 or biologically active portion thereof as compared to the known compound.

In another embodiment, an assay is a cell-free assay comprising contacting GAVE10 protein or biologically active portion thereof with a test compound and determining the ability of the test compound to modulate (e.g., stimulate or inhibit) the activity of the GAVE10 protein or biologically active portion thereof. Determining the ability of the test compound to modulate the activity of GAVE10 can be accomplished, for example, by determining the ability of the GAVE10 protein to bind to a GAVE10 target molecule by one of the methods described above for determining direct binding. In an alternative embodiment, determining the ability of the test compound to modulate the activity of GAVE10 can be accomplished by determining the ability of the GAVE10 protein to further modulate a GAVE10 target molecule. For example, the catalytic/enzymatic activity of the target molecule on an appropriate substrate can be determined as described previously.

In yet another embodiment, the cell-free assay comprises contacting the GAVE10 protein or biologically active portion thereof with a known compound that binds GAVE10 to form an assay mixture, contacting the assay mixture with a test compound and determining the ability of the test compound to interact with a GAVE10 protein, wherein determining the ability of the test compound to interact with a GAVE10 protein comprises determining the ability of the GAVE10 protein preferentially to bind to or to modulate the activity of a GAVE10 target molecule.

Receptors can be activated by non-ligand molecules that necessarily do not inhibit ligand binding but cause structural changes in the receptor to enable G protein binding or, perhaps receptor aggregation, dimerization or clustering that can cause activation.

Thus, antibodies can be raised to the various portions of GAVE10 that are exposed at the cell surface. Those antibodies that activate a cell via the G protein cascade as determined by standard assays, such as monitoring cAMP levels or intracellular $Ca^{+2}$ levels, can be selected.

The antibodies can be made using known techniques. Because molecular mapping and particularly epitope mapping is involved, monoclonal antibodies probably are preferred. The monoclonal antibodies can be raised both to intact receptor expressed at the cell surface and peptides known to form at the cell surface. The method of Geysen et al., U.S. Pat. No. 5,998,577, can be practiced to obtain a plurality of relevant peptides.

Antibodies found to activate GAVE10 may be modified to minimize activities extraneous to GAVE10 activation, such as complement fixation. Thus, the antibody molecules can be truncated or mutated to minimize or to remove activities outside of GAVE10 activation. For example, for certain antibodies, only the antigen-binding portion is needed. Thus, the $F_c$ portion of the antibody can be removed.

Cells expressing GAVE10 are exposed to antibody to activate GAVE10. Activated cells then are exposed to various molecules with a view to identifying those that alter receptor activity, whether to higher activation levels or to lower activation levels. Molecules that achieve those goals then can be tested on cells expressing GAVE10 without antibody to observe the effect on non-activated cells. The target molecules then can be tested and modified as candidate drugs for the treatment of disorders associated with altered GAVE10 metabolism using known techniques.

The cell-free assays of the instant invention are amenable to use of both the soluble form an the membrane-bound form of GAVE10. In the case of cell-free assays comprising the membrane-bound form of GAVE10, it may be desirable to utilize a solubilizing agent such that the membrane-bound form of GAVE10 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton X-100, Triton X-114, Thesit® non-ionic polyoxyethylene detergent, isotridecylpoly(ethylene glycol ether)$_n$, 3-[(3-cholamidopropyl)dimethylammino]-1-propane sulfonate (CHAPS), 3-[(3-cholamidopropyl)dimethylammino]-2-hydroxy-1-propane sulfonate (CHAPS) or N-dodecyl-N,N-dimethyl-3-ammonio-1-propane sulfonate.

In more than one embodiment of the above assay methods of the instant invention, it may be desirable to immobilize either GAVE10 or a target molecule thereof to facilitate separation of complexed from uncomplexed forms of one or both of the proteins, as well as to accommodate automation of the assay. Binding of a test compound to GAVE10 or interaction of GAVE10 with a target molecule in the presence and absence of a candidate compound, can be accomplished in any vessel suitable for containing the reactants. Examples of such vessels include microtitre plates, test tubes and microcentrifuge tubes. In one embodiment, a fusion protein can be provided that adds a domain that allows one or both of the proteins to be bound to a matrix. For example, glutathione-S-transferase/GAVE10 fusion proteins or glutathione-S-transferase/target fusion proteins can be adsorbed onto glutathione Sepharose® ion exchange media beads (Sigma Chemical, St. Louis, Mo.). Alternatively, glutathione-derivatized microtitre plates, that then are combined with the test compound or the test compound and either the non-adsorbed target protein or GAVE10 protein and the mixture incubated tinder conditions conducive to complex formation (e.g., at physiological conditions for salt and pH) can be used. Following incubation, the beads or microtitre plate wells are washed to remove any unbound components and complex formation is measured either directly or indirectly, for example, as described above. Alternatively, the complexes can be dissociated from the matrix and the level of GAVE10 binding or activity determined using standard techniques.

Other techniques for immobilizing proteins on matrices also can be used in the screening assays of the invention. For example, either GAVE10 or a target molecule thereof can be immobilized utilizing conjugation of biotin and streptavidin. Biotinylated GAVE10 or target molecules can be prepared from biotin-NHS (N-hydroxy-succinimide) using techniques well known in the art (e.g., biotinylation kit, Pierce Chemicals, Rockford, Ill.) and immobilized in the wells of streptavidin-coated 96-well plates (Pierce Chemicals). Alternatively, antibodies reactive with GAVE10 or target molecules but that do not interfere with binding of the GAVE10 protein to a target molecule can be derivatized to the wells of the plate and unbound target or GAVE10 trapped in the wells by antibody conjugation. Methods for detecting such complexes, in addition to those described above for the GST-immobilized complexes, include immunodetection of complexes using antibodies reactive with GAVE10 or target molecule, as well as enzyme-linked assays that rely on detecting an enzymatic activity associated with the GAVE10 or target molecule.

In another embodiment, modulators of GAVE10 expression are identified in a method in that a cell is contacted with a candidate compound and the expression of GAVE10 mRNA or protein in the cell is determined. The level of expression of GAVE10 mRNA or protein in the presence of the candidate compound is compared to the level of expression of GAVE10 mRNA or protein in the absence of the candidate compound. The candidate compound then can be identified as a modulator of GAVE10 expression based on that comparison. For example, when expression of GAVE10 mRNA or protein is greater (statistically significantly greater) in the presence of the candidate compound than in the absence thereof, the candidate compound is identified as a stimulator or agonist of GAVE10 mRNA or protein expression. Alternatively, when expression of GAVE10 mRNA or protein is less (statistically significantly less) in the presence of the candidate compound than in the absence thereof, the candidate compound is identified as an inhibitor or antagonist of GAVE10 mRNA or protein expression. If GAVE10 activity is reduced in the presence of ligand or agonist, or in a constitutive GAVE10, below baseline, the candidate compound is identified as an inverse agonist. The level of GAVE10 mRNA or protein expression in the cells can be determined by methods described herein for detecting GAVE10 mRNA or protein.

In yet another aspect of the invention, the GAVE10 proteins can be used as "bait proteins" in a two-hybrid assay or three-hybrid assay (see, e.g., U.S. Pat. No. 5,283,317; Zervos et al., Cell (1993) 72:223-232; Madura et al., J Biol Chem (1993) 268:12046-12054; Bartel et al., Bio/Techniques (1993) 14:920-924; Iwabuchi et al., Oncogene (1993) 8:1693-1696; and PCT Publication No. WO 94/10300), to identify other proteins, that bind to or interact with GAVE10 ("GAVE10-binding proteins" or "GAVE10-bp") and modulate GAVE10 activity. Such GAVE10-binding proteins also likely are involved in the propagation of signals by the GAVE10 proteins as, for example, upstream or downstream elements of the GAVE10 pathway.

As large quantities of pure GAVE10 can be made, physical characterization of the conformation of areas of likely function can be ascertained for rational drug design. For example, the IC3 region of the molecule and EC domains are regions of particular interest. Once the shape and ionic configuration of a region is discerned, candidate drugs that should interact with those regions can be configured and then tested in intact cells, animals and patients. Methods that would enable deriving such 3-D structure information include X-ray crystallography, NMR spectroscopy, molecular modeling and so on. The 3-D structure also can lead to identification of analogous conformational sites in other known proteins where known drugs that act at site exist. Those drugs, or derivatives thereof, may find use with GAVE10.

The invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, the sequences can be used to: (i) map the respective genes on a chromosome and, thus, locate gene regions associated with genetic disease; (ii) identify an individual from a minute biological sample (tissue typing); and (iii) aid in forensic identification of a biological sample. The applications are described in the subsections below.

1. Chromosome Mapping

Once the sequence (or a portion of the sequence) of a gene has been isolated, the sequence can be used to map the location of the GAVE10 gene on a chromosome, such as chromosome 2. Accordingly, GAVE10 nucleic acid molecules described herein or fragments thereof can been used to map the location of GAVE10 on chromosome 2. The mapping of the GAVE10 sequences to chromosome 2 is an important first step in correlating the sequences with genes associated with disease.

Briefly, GAVE10 genes can be mapped to chromosome 2 by preparing PCR primers (preferably 15-25 bp in length) from the GAVE10 sequences. The primers are used for PCR screening of somatic cell hybrids containing individual human chromosomes. Only those hybrids containing the human gene corresponding to the GAVE10 sequences yield an amplified fragment.

Somatic cell hybrids are prepared by fusing somatic cells from different mammals (e.g., human and mouse cells). As hybrids of human and mouse cells grow and divide, generally human chromosomes are lost in random order, but retain the mouse chromosomes are retained. By using media in that mouse cells cannot grow (because of lack of a particular enzyme), but in that human cells can, the one human chromosome that contains the gene encoding the needed enzyme will be retained. By using various media, panels of hybrid cell lines are established. Each cell line in a panel contains either a single human chromosome or a small number of human chromosomes and a full set of mouse chromosomes, allowing easy mapping of individual genes to specific human chromosomes. (D'Eustachio et al., Science (1983) 220:919-924). Somatic cell hybrids containing only fragments of human chromosomes also can be produced by using human chromosomes with translocations and deletions.

PCR mapping of somatic cell hybrids is a rapid procedure for assigning a particular sequence to a particular chromosome. Three or more sequences can be assigned per day using a single thermocycler. Using the GAVE10 sequences to design oligonucleotide primers, sublocalization is achieved with panels of fragments of or translocations involving chromosome 2. Other mapping strategies that can similarly be used to map a GAVE10 sequence to chromosome 2 include in situ hybridization (described in Fan et al., Proc Natl Acad Sci USA (1990) 87:6223-27), pre-screening with labeled flow-sorted chromosomes and pre-selection by hybridization to chromosome-specific cDNA libraries.

Fluorescence in situ hybridization (FISH) of a DNA sequence to a metaphase chromosomal spread further can be used to provide a precise chromosomal location in one step. Chromosome spreads can be made using cells wherein division has been blocked in metaphase by a chemical, e.g., colcemid, that disrupts the mitotic spindle. The chromosomes can be treated briefly with trypsin and then stained with example, GAVE10 tentatively is mapped to 12q24.23 by in silico mapping.

Reagents for chromosome mapping can be used individually to mark chromosome 2 or a single site on a chromosome or panels of reagents can be used for marking multiple sites and/or multiple chromosomes. Reagents corresponding to flanking regions of the GAVE10 gene actually are preferred for mapping purposes. Coding sequences are more likely to be conserved within gene families, thus increasing the chance of cross hybridization during chromosomal mapping.

Once a sequence has been mapped to a precise chromosomal location, the physical position of the sequence on the chromosome can be correlated with genetic map data. (Such data are found, for example, in McKusick, Mendelian Inheritance in Man, available on-line through Johns Hopkins University, Welch Medical Library). The relationship between genes and disease, mapped to the same chromosomal region, then can be identified through linkage analysis (co-inheritance of physically adjacent genes), described in, e.g., Egeland et al., Nature (1987) 325:783-787.

Moreover, differences in the DNA sequences between individuals affected and unaffected with a disease associated with GAVE10 can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The GAVE10 sequences of the instant invention also can be used to identify individuals from minute biological samples. The United States military, for example, is considering the use of restriction fragment length polymorphism (RFLP) for identification of personnel. In the technique, genomic DNA of an individual is digested with one or more restriction enzymes and probed on a Southern blot to yield unique bands for identification. The method does not suffer from the current limitations of "Dog Tags" that can be lost, switched or stolen, making positive identification difficult. The sequences of the instant invention are useful as additional DNA markers for RFLP (described in U.S. Pat. No. 5,272,057).

Furthermore, the sequences of the instant invention can be used to provide an alternative technique that determines the actual base-by-base DNA sequence of selected portions of the genome of an individual. Thus, the GAVE10 sequences described herein can be used to prepare two PCR primers from the 5' and 3' ends of the sequences. The primers then can be used to amplify the DNA of an individual and subsequently provide a sequence thereof.

Panels of corresponding DNA sequences from individuals, prepared in that manner, can provide unique individual identifications, as each individual will have a unique set of such DNA sequences due to allelic differences. The sequences of the instant invention can be used to obtain such identification sequences from individuals and from tissue. The GAVE10 sequences of the invention uniquely represent portions of the human genome. Allelic variation occurs to some degree in the coding regions of the sequences and to a greater degree in the noncoding regions. It is estimated that allelic variation between individual humans occurs with a frequency of about once per each 500 bases. Each of the sequences described herein can, to some degree, be used as a standard against that DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers that each yield a non-coding amplified sequence of 100 bases. If predicted coding sequences, such as those in SEQ ID NO:1 are used, a more appropriate number of primers for positive individual identification would be 500-2,000.

If a panel of reagents from GAVE10 sequences described herein is used to generate a unique identification database for an individual, those same reagents can later be used to identify tissue from that individual. Using the unique identification database, positive identification of the individual, living or dead, can be made from extremely small tissue samples.

3. Use of Partial GAVE10 Sequences in Forensic Biology

DNA-based identification techniques also can be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva or semen found at a crime scene. The amplified sequence then can be compared to a standard, thereby allowing identification of the origin of the biological sample.

The sequences of the instant invention can be used to provide polynucleotide reagents, e.g., PCR primers, targeted to specific loci in the human genome, that can enhance the reliability of DNA-based forensic identifications. For example, a nucleic acid of interest can provide another "identification marker" (i.e., another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for that use as greater numbers of polymorphisms occur in the noncoding regions, enhancing discrimination to differentiate individuals using that technique. Examples of polynucleotide reagents include the GAVE10 sequences or portions thereof; e.g., fragments derived from the noncoding regions of SEQ ID NO:1 having a length of at least 20 or 30 bases.

The GAVE10 sequences described herein further can be used to provide polynucleotide reagents, e.g., labeled or labelable probes that can be used in, for example, an in situ hybridization technique, to identify a specific tissue, e.g., brain tissue. That can be very useful in cases where a forensic pathologist is presented with a tissue of unknown origin. Panels of such GAVE10 probes can be used to identify tissue by species and/or by organ type.

In a similar fashion, the reagents, e.g., GAVE10 primers or probes, can be used to screen tissue culture for contamination (i.e., screen for the presence of a mixture of different types of cells in a culture).

C. Predictive Medicine

The instant invention also pertains to the field of predictive medicine in that diagnostic assays, prognostic assays, pharmacogenomics and monitoring clinical trials are used for prognostic (predictive) purposes to treat an individual prophylactically. Accordingly, one aspect of the instant invention relates to diagnostic assays for determining GAVE10 protein and/or nucleic acid expression as well as GAVE10 activity, in the context of a biological sample (e.g., blood, urine, feces, sputum, serum, cells and tissue). The assay can be used to determine whether an individual is afflicted with a disease or disorder, or is at risk of developing a disorder, associated with aberrant GAVE10 expression or activity.

The invention also provides for prognostic (or predictive) assays for determining whether an individual is at risk of developing a disorder associated with GAVE10 protein, nucleic acid expression or activity. For example, mutations in a GAVE10 gene can be assayed in a biological sample. Such assays can be used for prognostic or predictive purpose thereby to treat prophylactically an individual prior to the onset of a disorder characterized by or associated with GAVE10 protein, nucleic acid expression or activity.

Another aspect of the invention provides methods for determining GAVE10 protein, nucleic acid expression or GAVE10 activity in an individual thereby to select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Yet another aspect of the invention pertains to monitoring the influence of agents (e.g., drugs or other compounds) on the expression or activity of GAVE10 in clinical trials.

Those and other agents are described in further detail in the following sections.

1. Diagnostic Assays

An exemplary method for detecting the presence or absence of GAVE10 in a biological sample involves obtaining a biological sample from a test subject and contacting the biological sample with a compound or an agent capable of detecting GAVE10 protein or nucleic acid (e.g., mRNA or genomic DNA) that encodes GAVE10 protein such that the presence of GAVE10 is detected in the biological sample. A preferred agent for detecting GAVE10 mRNA or genomic DNA is a labeled nucleic acid probe capable of hybridizing to GAVE10 mRNA or genomic DNA. The nucleic acid probe can be, for example, a full-length GAVE10 nucleic acid, such as the nucleic acid of SEQ ID NO:1 or a portion thereof, such as an oligonucleotide of at least 15, 30, 50, 100, 250 or 500 or more nucleotides in length and sufficient to specifically hybridize under stringent conditions to GAVE10 mRNA or genomic DNA. Other suitable probes for use in the diagnostic assays of the invention are described herein.

A preferred agent for detecting GAVE10 protein is an antibody capable of binding to GAVE10 protein, preferably an antibody with a detectable label. Antibodies can be polyclonal or more preferably, monoclonal. An intact antibody or a fragment thereof (e.g., $F_{ab}$ or $F_{(ab')2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is labeled directly. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect GAVE10 mRNA, protein or genomic DNA in a biological sample in vitro as well as in vivo. For example, in vitro techniques for detection of GAVE10 mRNA include Northern hybridization and in situ hybridization. In vitro techniques for detection of GAVE10 protein include ELISA, Western blot, immunoprecipitation and immunofluorescence. In vitro techniques for detection of GAVE10 genomic DNA include Southern hybridization. Furthermore, in vivo techniques for detection of GAVE10 protein include introducing into a subject a labeled anti-GAVE10 antibody. For example, the antibody can be labeled with a radioactive marker, the presence and location of which in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

Hence, association with a disease and identification of nucleic acid or protein polymorphism diagnostic for the carrier or the affected can be beneficial in developing prognostic or diagnostic assays. For example, it would be beneficial to have a prognostic or diagnostic assay for rheumatoid arthritis, asthma, Crohn's Disease and so on. GAVE10 expression is elevated in cells associated with activated or inflammatory states. Disorders associated with inflammation include, anaphylactic states, colitis, Crohn's Disease, edematous states, contact hypersensitivity, allergy, other forms of arthritis, meningitis and other conditions wherein the immune system reactes to an insult by vascular dilation, heat, collecting cells, fluids and the like at a site resulting in swelling and the like. Thus, a disorder in GAVE10 metabolism may be diagnostic for rheumatoid arthritis. Moreover, the molecular mechanism of rheumatoid arthritis may be detectable, such as, there may be a diagnostic SNP, RFLP, variability of expression level, variability of function and so on that can be detectable in a tissue sample, such as a blood sample.

In another embodiment, the methods further involve obtaining a biological sample from a control subject, contacting the control sample with a compound or agent capable of detecting GAVE10 protein, mRNA or genomic DNA, such that the presence and amount of GAVE10 protein, mRNA or genomic DNA is detected in the biological sample, and comparing the presence and amount of GAVE10 protein, mRNA or genomic DNA in the control sample with the presence and amount of GAVE10 protein, mRNA or genomic DNA in a test sample.

The invention also encompasses kits for detecting the presence of GAVE10 in a biological sample (a test sample). Such kits can be used to determine if a subject is suffering from or is at increased risk of developing a disorder associated with aberrant expression of GAVE10 (e.g., an immunological disorder). For example, the kit can comprise a labeled compound or agent capable of detecting GAVE10 protein or mRNA in a biological sample and means for determining the amount of GAVE10 in the sample (e.g., an anti-GAVE10 antibody or an oligonucleotide probe that binds to DNA encoding GAVE10, e.g., SEQ ID NO:1). Kits also can be used to yield results indicating whether the tested subject is suffering from or is at risk of developing a disorder associated with aberrant expression of GAVE10, if the amount of GAVE10 protein or mRNA is above or below a normal level.

For antibody-based kits, the kit can comprise, for example: (1) a first antibody (e.g., attached to a solid support) that binds to GAVE10 protein; and, optionally, (2) a second, different antibody that binds to GAVE10 protein or to the first antibody and is conjugated to a detectable agent. If the second antibody is not present, either another molecule that binds the first antibody, that can be labeled, can be used or the first antibody is labeled. In any event, a labeled binding moiety is included to serve as the detectable reporter molecule, as known in the art.

For oligonucleotide-based kits, the kit can comprise, for example: (1) an oligonucleotide, e.g., a detectably-labeled oligonucleotide, that hybridizes to a GAVE10 nucleic acid sequence or (2) a pair of primers useful for amplifying a GAVE10 nucleic acid molecule.

The kit also can comprise, e.g., a buffering agent, a preservative or a protein stabilizing agent. The kit also can comprise components necessary for detecting the detectable agent (e.g., an enzyme or a substrate). The kit also can contain a control sample or a series of control samples that can be assayed and compared to the test sample. Each component of the kit usually is enclosed within an individual container and all of the various containers are within a single package along with instructions for observing whether the tested subject is suffering from or is at risk of developing a disorder associated with aberrant expression of GAVE10.

2. Prognostic Assays

The methods described herein furthermore can be utilized as diagnostic or prognostic assays to identify subjects having or are at risk of developing a disease or disorder associated with aberrant GAVE10 expression or activity. For example, the assays described herein, such as the preceding diagnostic assays or the following assays, can be utilized to identify a subject having or is at risk of developing a disorder associated with GAVE10 protein, nucleic acid expression or activity. For example, recent contact with bacteria or inflammation associated with asthma, chronic obstructive pulmonary disease and rheumatoid arthritis are amenable for assay. Alternatively, the prognostic assays can be utilized to identify a subject having or is at risk for developing such a disease or disorder.

Thus, the instant invention provides a method in which a test sample is obtained from a subject and GAVE10 protein or nucleic acid (e.g., mRNA or genomic DNA) is detected. The presence of GAVE10 protein or nucleic acid is diagnostic of a subject having or is at risk of developing a disease or disorder associated with aberrant GAVE10 expression or activity. As used herein, a "test sample" refers to a biological sample obtained from a subject of interest. For example, a test sample can be a biological fluid (e.g., serum), cell sample or tissue.

Furthermore, the prognostic assays described herein can be used to determine whether a subject can be administered an agent (e.g., an agonist, antagonist, peptidomimetic, protein, peptide, nucleic acid, small molecule or other drug candidate) to treat a disease or disorder associated with aberrant GAVE10 expression or activity. For example, such methods can be used to determine whether a subject can be treated effectively with a specific agent or class of agents (e.g., agents of a type that decrease GAVE10 activity). Thus, the instant invention provides methods for determining whether a subject can be treated effectively with an agent for a disorder associated with aberrant GAVE10 expression or activity in that a test sample is obtained and GAVE10 protein or nucleic acid is detected (e.g., wherein the presence of GAVE10 protein or nucleic acid is diagnostic of a subject that can be administered the agent to treat a disorder associated with aberrant GAVE10 expression or activity).

The methods of the invention also can be used to detect genetic lesions or mutations in a GAVE10 gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion or mutation characterized by at least one of an alteration affecting the integrity of a gene encoding a GAVE10-protein or the mis-expression of the GAVE10 gene. For example, such genetic lesions or mutations can be detected by ascertaining the existence of at least one of: 1) a deletion of one or more nucleotides from a GAVE10 gene; 2) an addition of one or more nucleotides to a GAVE10 gene; 3) a substitution of one or more nucleotides of a GAVE10 gene; 4) a chromosomal rearrangement involving a GAVE10 gene; 5) an alteration in the level of a messenger RNA transcript of a GAVE10 gene; 6) an aberrant modification of a GAVE10 gene, such as of the methylation pattern of the genomic DNA; 7) a non-wild type level of a GAVE10 protein; 8) an allelic loss of a GAVE10 gene; and 9) an inappropriate post-translational modification of a GAVE10 protein. As described herein, there are a large number of assay techniques known in the art that can be used for detecting lesions in a GAVE10 gene. A preferred biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al., Science (1988) 241:1077-1080; and Nakazawa et al., Proc Natl Acad Sci USA (1994) 91:360-364), the latter of which can be particularly useful for detecting point mutations in the GAVE10 gene (see, e.g., Abravaya et al., Nucleic Acids Res (1995) 23:675-682). The method can include the steps of collecting a sample of cells from a patient, isolating nucleic acid (e.g., genomic, mRNA or both) from the cells of the sample, contacting the nucleic acid sample with one or more primers that specifically hybridize to a GAVE10 gene under conditions such that hybridization and amplification of the GAVE10 gene (if present) occurs and detecting the presence or absence of an amplification product or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli et al., Proc Natl Acad Sci USA (1990) 87:1874-1878), transcriptional amplification system (Kwoh et al., Proc Natl Acad Sci USA (1989) 86:1173-1177), Q-β replicase (Lizardi et al., Bio/Technology (1988) 6:1197) or any other nucleic acid amplification method, followed by the detection of the amplified molecules using techniques well known to those of skill in the art. The detection schemes are especially useful for the detection of nucleic acid molecules if such molecules are present in very low numbers.

In an alternative embodiment, mutations in a GAVE10 gene from a sample cell can be identified by alterations in restriction enzyme cleavage patterns. For example, sample and control DNA is isolated, amplified (optionally), digested with one or more restriction endonucleases and fragment length sizes are determined by gel electrophoresis and compared. Differences in fragment length sizes between sample and control DNA indicate mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in GAVE10 can be identified by hybridizing a sample and control nucleic acids, e.g., DNA or RNA, to high density arrays containing hundreds or thousands of oligonucleotides probes (Cronin et al., Human Mutation (1996) 7:244-255; Kozal et al., Nature Medicine (1996) 2:753-759). For example, genetic mutations in GAVE10 can be identified in two-dimensional arrays containing light-generated DNA probes as described in Cronin et al., supra. Briefly, a first hybridization array of probes can be used to scan through long stretches of DNA in a sample and control to identify base changes between the sequences by generating linear arrays of sequential overlapping probes. That step allows the identification of point mutations. The step is followed by a second hybridization array that allows the characterization of specific mutations by using smaller, specialized probe arrays complementary to all variants or mutations detected. Each mutation array is composed of parallel probe sets, one complementary to the wild type gene and the other complementary to the mutant gene.

In yet another embodiment, any of a variety of sequencing reactions known in the art can be used to directly sequence the GAVE10 gene and detect mutations by comparing the sequence of the sample GAVE10 with the corresponding wild type (control) sequence. Examples of sequencing reactions include those based on techniques developed by Maxam & Gilbert (Proc Natl Acad Sci USA (1977) 74:560) or Sanger (Proc Natl Acad Sci USA (1977) 74:5463). It also is contemplated that any of a variety of automated sequencing procedures can be utilized when performing the diagnostic assays (Bio/Techniques (1995) 19:448), including sequencing by mass spectrometry (see, e.g., PCT Publication No. WO 94/16101; Cohen et al., Adv Chromatogr (1996) 36:127-162; and Griffin et al., Appl Biochem Biotechnol (1993) 38:147-159).

Other methods for detecting mutations in the GAVE10 gene include methods in that protection from cleavage agents is used to detect mismatched bases in RNA/RNA or RNA/DNA heteroduplexes (Myers et al., Science (1985) 230:1242). In general, the technique of "mismatch cleavage" entails providing heteroduplexes formed by hybridizing (labeled) RNA or DNA containing the wild type GAVE10 sequence with potentially mutant RNA or DNA obtained from a tissue sample. The double-stranded duplexes are treated with an agent that cleaves single-stranded regions of the duplex such as that will exist due to base pair mismatches between the control and sample strands. RNA/DNA duplexes can be treated with RNase to digest mismatched regions and DNA/DNA hybrids can be treated with S1 nuclease to digest mismatched regions. In other embodiments, either DNA/DNA or RNA/DNA duplexes can be treated with hydroxylamine or osmium tetroxide and with piperidine to digest mismatched regions. After digestion of the mismatched regions, the resulting material then is separated by size on denaturing polyacrylamide gels to determine the site of mutation. See, e.g., Cotton et al., Proc Natl Acad Sci USA (1988) 85:4397; Saleeba et al., Methods Enzymol (1992) 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in GAVE10 cDNAs obtained from samples of cells. For example, the mutY enzyme of E. coli cleaves A at G/A mismatches and the thymidine DNA glycosylase from HeLa cells cleaves T at G/T mismatches (Hsu et al., Carcinogenesis (1994) 15:1657-1662). According to an exemplary embodiment, a probe based on a GAVE10 sequence, e.g., a wild type GAVE10 sequence, is hybridized to a cDNA or other DNA product from a test cell(s). The duplex is treated with a DNA mismatch repair enzyme and the cleavage products, if any, can be detected in electrophoresis protocols or the like, see, e.g., U.S. Pat. No. 5,459,039.

In other embodiments, alterations in electrophoretic mobility will be used to identify mutations in GAVE10 genes. For example, single-strand conformation polymorphism (SSCP) may be used to detect differences in electrophoretic mobility between mutant and wild type nucleic acids (Orita et al., Proc Natl Acad Sci USA (1989) 86:2766; see also Cotton, Mutat Res (1993) 285:125-144; Hayashi, Genet Anal Tech Appl (1992) 9:73-79). Single-stranded DNA fragments of sample and control GAVE10 nucleic acids will be denatured and allowed to renature. The secondary structure of single-stranded nucleic acids varies according to sequence and the resulting alteration in electrophoretic mobility enables the detection of even a single base change. The DNA fragments may be labeled or detected with labeled probes. The sensitivity of the assay may be enhanced by using RNA (rather than DNA) because the secondary structure of RNA is more sensitive to a change in sequence. In a preferred embodiment, the subject method utilizes heteroduplex analysis to separate double-stranded heteroduplex molecules on the basis of changes in electrophoretic mobility (Keen et al., Trends Genet (1991) 7:5).

In yet another embodiment, the movement of mutant or wild type fragments in polyacrylamide gels containing a gradient of denaturant is assayed using denaturing gradient gel electrophoresis (DGGE) (Myers et al., Nature (1985) 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum et al., Biophys Chem (1987) 265:12753).

Examples of other techniques for detecting point mutations include, but are not limited to, selective oligonucleotide hybridization, selective amplification or selective primer extension. For example, oligonucleotide primers may be prepared in that the known mutation is placed centrally and then hybridized to target DNA under conditions that permit hybridization only if a perfect match is found (Saiki et al., Nature (1986) 324:163); Saiki et al., Proc Natl Acad Sci USA (1989) 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al., Nucleic Acids Res (1989) 17:2437-2448) or at the extreme 3' end of one primer where, under appropriate conditions, mismatch can prevent or reduce polymerase extension (Prossner, Tibtech (1993) 11:238). In addition, it may be desirable to introduce a novel restriction site in the region of the mutation to create cleavage-based detection (Gasparini et al., Mol Cell Probes (1992) 6:1). It is anticipated that in certain embodiments amplification also may be performed using Taq ligase for amplification (Barany, Proc Natl Acad Sci USA (1991) 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein. The method and kit may be used conveniently, e.g., in clinical settings, to diagnose patients exhibiting symptoms or family history of a disease or illness involving a GAVE10 gene.

Furthermore, any cell type or tissue where GAVE10 is expressed may be utilized in the prognostic assays described herein.

3. Pharmacogenomics

Agents or modulators that have a stimulatory or inhibitory effect on GAVE10 activity (e.g., GAVE10 gene expression) as identified by a screening assay described herein can be administered to individuals to treat (prophylactically or therapeutically) disorders (e.g., inflammation associated with asthma, chronic obstructive pulmonary disease and rheumatoid arthritis) associated with GAVE10 activity. In conjunction with such treatment, the pharmacogenomics (i.e., the study of the relationship between the genotype of an individual and the response of the individual to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the genotype of the individual. Such pharmacogenomics further can be used to determine appropriate dosages and therapeutic regimens. Accordingly, the activity of GAVE10 protein, expression of GAVE10 nucleic acid or mutation content of GAVE10 genes in an individual can be determined thereby to select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder, Clin Chem (1997) 43(2):254-266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism." The pharmacogenetic conditions can occur either as rare defects or as polymorphisms. For example, glucose-6-phosphate dehydrogenase deficiency (G6PD) is a common inherited enzymopathy in that the main clinical complication is hemolysis after ingestion of oxidant drugs (anti-malarials, sulfonamides, analgesics or nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes, CYP2D6 and CYP2C19) has provided an explanation as to why some patients do not obtain the expected drug effects or show exaggerated drug response and serious toxicity after taking the standard and safe dose of a drug. The polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, all which lead to the absence of functional CYP2D6. Poor metabolizers of CYP2D6 and CYP2C19 quite frequently experience exaggerated drug response and side effects when standard doses are received. If a metabolite is the active therapeutic moiety, a PM will show no therapeutic response, as demonstrated for the analgesic effect of codeine mediated by the CYP2D6-formed metabolite, morphine. The other extreme is the so-called ultra-rapid metabolizers who do not respond to standard doses. Recently, the molecular basis of ultra-rapid metabolism has been identified to be due to CYP2D6 gene amplification.

Thus, the activity of GAVE10 protein, expression of GAVE10 nucleic acid or mutation content of GAVE10 genes in an individual can be determined to select thereby appropriate agent(s) for therapeutic or prophylactic treatment of the individual. In addition, pharmacogenetic studies can be used to apply genotyping of polymorphic alleles encoding drug-metabolizing enzymes to the identification of the drug responsiveness phenotype of an individual. That knowledge, when applied to dosing or drug selection, can avoid adverse reactions or therapeutic failure and thus enhance therapeutic or prophylactic efficiency when treating a subject with a GAVE10 modulator, such as a modulator identified by one of the exemplary screening assays described herein.

4. Monitoring of Effects During Clinical Trials

Monitoring the influence of agents (e.g., drugs or compounds) on the expression or activity of GAVE10 (e.g., the ability to modulate aberrant cell proliferation and/or differentiation) can be applied not only in basic drug screening, but also in clinical trials. For example, the effectiveness of an agent, as determined by a screening assay as described herein, to increase GAVE10 gene expression, protein levels or protein activity, can be monitored in clinical trials of subjects exhibiting decreased GAVE10 gene expression, protein levels or protein activity. Alternatively, the effectiveness of an agent, as determined by a screening assay, to decrease GAVE10 gene expression, protein levels or protein activity, can be monitored in clinical trials of subjects exhibiting increased GAVE10 gene expression, protein levels or protein activity. In such clinical trials, GAVE10 expression or activity and preferably, that of other genes that have been implicated in, for example, a cellular proliferation disorder, can be used as a marker of the immune responsiveness of a particular cell.

For example, and not by way of limitation, genes, including GAVE10, that are modulated in cells by treatment with an agent (e.g., compound, drug or small molecule) that modulates GAVE10 activity (e.g., as identified in a screening assay described herein) can be identified. Thus, to study the effect of agents on cellular proliferation disorders, for example, in a clinical trial, cells can be isolated and RNA prepared and analyzed for the levels of expression of GAVE10 and other genes implicated in the disorder. The levels of gene expression (i.e., a gene expression pattern) can be quantified by Northern blot analysis or RT-PCR, as described herein, or alternatively by measuring the amount of protein produced by one of the methods as described herein or by measuring the levels of activity of GAVE10 or other genes. In that way, the gene expression pattern can serve as a marker, indicative of the physiological response of the cells to the agent. Accordingly, the response state may be determined before and at various points during treatment of the individual with the agent.

In a preferred embodiment, the instant invention provides a method for monitoring the effectiveness of treatment of a subject with an agent (e.g., an agonist, antagonist, peptidomimetic, protein, peptide, nucleic acid, small molecule or other drug candidate identified by the screening assays described herein) comprising the steps of (i) obtaining a pre-administration sample from a subject prior to administration of the agent; (ii) detecting the level of expression of a GAVE10 protein, mRNA or genomic DNA in the preadministration sample; (iii) obtaining one or more post-administration samples from the subject; (iv) detecting the level of expression or activity of the GAVE10 protein, mRNA or genomic DNA in the post-administration samples; (v) comparing the level of expression or activity of the GAVE10 protein, mRNA or genomic DNA in the pre-administration sample with the GAVE10 protein, mRNA or genomic DNA in the post-administration sample or samples; and (vi) altering the administration of the agent to the subject accordingly. For example, increased administration of the agent may be desirable to increase the expression or activity of GAVE10 to higher levels than detected, i.e., to increase the effectiveness of the agent. Alternatively, decreased administration of the agent may be desirable to decrease expression or activity of GAVE10 to lower levels than detected, i.e., to decrease the effectiveness of the agent.

D. Methods of Treatment

The instant invention provides for both prophylactic and therapeutic methods of treating a subject at risk of (or susceptible to) a disorder or having a disorder associated with aberrant GAVE10 expression or activity. Such disorders include, but are not limited to, for example, inflammatory disorders such as asthma, chronic obstructive pulmonary disease and rheumatoid arthritis.

1. Prophylactic Methods

In one aspect, the invention provides a method for preventing in a subject, a disease or condition associated with an aberrant GAVE10 expression or activity, by administering to the subject an agent that modulates GAVE10 expression or at least one GAVE10 activity. Subjects at risk for a disease that is caused by or contributed to by aberrant GAVE10 expression or activity can be identified by, for example, any or a combination of diagnostic or prognostic assays as described herein. Administration of a prophylactic agent can occur prior to the manifestation of symptoms characteristic of the GAVE10 aberrancy, such that a disease or disorder is prevented or, alternatively, delayed in progression. Depending on the type of GAVE10 aberrancy, for example, a GAVE10 agonist or GAVE10 antagonist agent can be used for treating the subject. The appropriate agent can be determined based on screening assays described herein.

2. Therapeutic Methods

Another aspect of the invention pertains to methods of modulating GAVE10 expression or activity for therapeutic purposes. The modulatory method of the invention involves contacting a cell with an agent that modulates one or more of the activities of GAVE10 protein activity associated with the cell. An agent that modulates GAVE10 protein activity can be an agent as described herein, such as a nucleic acid or a protein, a naturally-occurring cognate ligand of a GAVE10 protein, a peptide, a GAVE10 peptidomimetic or other small molecule. In one embodiment, the agent stimulates one or more of the biological activities of GAVE10 protein. Examples of such stimulatory agents include active GAVE10 protein and a nucleic acid molecule encoding GAVE10 that has been introduced into the cell. In another embodiment, the agent inhibits one or more of the biological activities of GAVE10 protein. Examples of such inhibitory agents include antisense GAVE10 nucleic acid molecules and anti-GAVE10 antibodies. The modulatory methods can be performed in vitro (e.g., by culturing the cell with the agent) or, alternatively, in vivo (e.g., by administering the agent to a subject). As such, the instant invention provides methods of treating an individual afflicted with a disease or disorder characterized by aberrant expression or activity of a GAVE10 protein or nucleic acid molecule. In one embodiment, the method involves administering an agent (e.g., an agent identified by a screening assay described herein) or combination of agents that modulates (e.g., upregulates or downregulates) GAVE10 expression or activity. In another embodiment, the method involves administering a GAVE10 protein or nucleic acid molecule as therapy to compensate for reduced or aberrant GAVE10 expression or activity.

Stimulation of GAVE10 activity is desirable in situations in that GAVE10 is downregulated abnormally and/or in that increased GAVE10 activity is likely to have a beneficial effect. Conversely, inhibition of GAVE10 activity is desirable in situations in that GAVE10 is upregulated abnormally and/or in that decreased GAVE10 activity is likely to have a beneficial effect.

The invention is illustrated further by the following examples that should not be construed as limiting. The contents of all references, patents and published patent applications cited throughout the application hereby are incorporated by reference.

EXAMPLE 1

Cloning hGAVE10 cDNA

Human genome banks were mined for GPCR motifs. A human genomic DNA, AC021016.3, gi7630969, was selected. The genomic DNA, and fragments thereof, could be used as probe in Northern blots.

PCR screening is performed on a pool of human kidney, thymus and placenta cDNA libraries. Primers for PCR are designed using the following sequences:

```
                                            (SEQ ID NO:6)
Forward:          5'-CAGGACCAAGATGACGCCCA-3'

(SEQ ID NO:7)
Nested Forward:   5'-CGAAGCTTCAGGACCAAGATGAGC-3'
```

The nested forward primer contains a HindIII restriction enzyme site followed by a Kozak sequence. The nested reverse primer contains an XhoI restriction enzyme site. PCR is carried out in a Biometra Trio-Thermoblock thermocycler, using Pfu DNA polymerase (Stratagene) that is added to the PCR reaction following addition of template cDNA, primers, Pfu buffer and dNTP. The 50 µl reaction contains: 5 µl of 10×Pfu DNA buffer, 2 µl (2500 units/ml) of Pfu DNA polymerase, 1.0 µl of NTP mixture (containing 10 mM of each nucleotide); 2.0 µl of forward primer (10 mM); 2.0 µl of reverse primer (10 mM); 5 µl cDNA template and 33 µl sterile water. The following cycles were used in the thermocycler: 94° C. for 2 minutes, followed by 30 cycles of 94° C. for 45 seconds, 58° C. for 45 seconds, 72° C. for 3 minutes, 72° C. for 10 minutes; and cooling down at 4° C.

Following PCR, 3 µl of dNTP (10 mM of each nucleotide) Clontech Catalog No. 7404-i and 1 µl (5 units) of Taq DNA Polymerase (Qiagen, Catalog No. 201223) are added to the PCR product and the mixture is incubated at 72° C. for 10 minutes. The PCR product then is run on a 1% agarose gel. About a 1 kilobase band containing the desired fragment is cut from the gel and purified using the Qiaquick Gel Extraction Kit using the protocol provided by the manufacturer (Qiagen, Catalog No. 28704). The purified PCR product then is subcloned into a pCR2.1 vector (Invitrogen, Catalog Nos. K2000-01/40/J10 and K2030-01/40/J10). To subclone the PCR product into the pCR2.1 vector, a ligation reaction is prepared using an Invitrogen TA cloning vector kit. The ligation reaction contained: 5 µl sterile water; 1 µl Invitrogen 2× ligation buffer; 2 µl pCR2.1 vector (25 ng/µl); 4 µl PCR product DNA (10 ng); 4 µl (5×) dilution buffer; and 1 µl T4 DNA ligase (5 units). The reaction is incubated for 18 hours at 14° C. E. coli cells are transformed with the ligation reaction by mixing 2 µl of the ligation reaction mixture with 200 µl of INVα F' competent E. coli cells (Invitrogen Catalog No. C658-00), incubation on ice for 30 minutes, heat shock at 37° C. for 45 seconds and incubation on ice for 2 minutes followed by addition of 800 µl of LB. The cells then are incubated overnight at 37° C. with agitation in a bacterial shaker/incubator (air is re-circulated). Following the overnight incubation, 200 µl of the transformation reaction mixture is plated onto LB agar plates containing 100 µg/ml ampicillin and incubated overnight at 37° C.

Following the incubation, colonies are picked and each individual colony is grown in a separate tube overnight in 500 µl of LB containing 100 µg/ml ampicillin in a shaker/incubator. To screen colonies by PCR, the following reaction is used: 41.5 µl of a colony in LB; 5 µl Taq buffer (10×); 1.0 µl dNTP (10 mM of each nucleotide); 1.0 µl forward primer (10 mM); 1.0 µl reverse primer (10 mM); and 0.5 µl Taq DNA polymerase (5 units/µl).

The reaction is incubated in a thermocycler using the following cycles: 94° C. for 2 minutes, 94° C. for 30 seconds, 55° C. for 30 seconds, 72° C. for 1 minute and 72° C. for 10 minutes, followed by cooling down at 4° C.

To check the results of the PCR reaction, 5 µl of the PCR reaction is run on 1% TAB agarose gel. Positive clones showed an insert of about 1 kb. Positive clones are grown in 5 ml LB+100 µg/ml ampicillin overnight at 37° C. in a bacterial shaker/incubator. The plasmid is purified using a Qiagen DNA purification column as instructed in the manufacturer protocol (Qiagen Catalog No. 12143). The positive clones then are sequenced using a T7 forward primer (5'-GGCTC-CCAACTTCTCTTC-3') (SEQ ID NO:8) and an M13 reverse primer (5'-GGGCAGTGGCCAGCACGC-3') (SEQ ID NO:9). DNA sequencing identified isolation of a cDNA having the DNA sequence presented in FIG. 1 (SEQ ID NO:1) and the amino acid sequence presented in FIG. 2 (SEQ ID NO:2).

EXAMPLE 2

Generation of Mammalian Cells Overexpressing hGAVE10

To provide significant quantities of hGAVE10 for further experiments, the cDNA encoding hGAVE10 is cloned into an expression vector and transfected into mammalian cells, such as 293 cells.

To generate mammalian cells overexpressing hGAVE10, mammalian cells are plated in a six-well 35 mm tissue culture plate ($3\times10^5$ mammalian cells per well (ATCC Catalog No. CRL-1573)) in 2 ml of DMEM media (Gibco/BRL, Catalog No. 11765-054) in the presence of 10% fetal bovine serum (Gibco/BRL Catalog No. 1600-044).

The cells then are incubated at 37° C. in a $CO_2$ incubator until the cells are 50-80% confluent. The cloned cDNA nucleic acid sequence of hGAVE10 is inserted using the procedure described above in a pcDNA 3.1 cloning vector (Invitrogen, Catalog No. V790-20). Two µg of the DNA are diluted into 100 µl of serum-free F12 HAM media. Separately, 25 µl of Lipofectamine Reagent (Life Technologies, Catalog No. 18324-020) is diluted into 100 µl of serum-free F12 HAM media. The DNA solution and the Lipofectamine solution then are mixed gently and incubated at room temperature for 45 minutes to allow for the formation of DNA-lipid complexes.

The cells are rinsed once with 2 ml of serum-free F12 HAM media. For each transfection (six transfections in a six-well plate), 0.8 ml of serum-free F12 HAM media are added to the solution containing the DNA-lipid complexes (0.2 ml total volume) and mixed gently. The resulting mixture (hereinafter the "transfection mixture") then is overlaid (0.8 ml+0.2 ml) onto the rinsed cells. No anti-bacterial reagents are added. The cells then are incubated with the lipid-DNA complexes for 16 hours at 37° C. in a $CO_2$ incubator to allow for transfection.

After the completion of the incubation period, 1 ml of F12 HAM media containing 10% fetal bovine serum is overlaid onto the cells without first removing the transfection mixture. At 18 hours after transfection, the media overlaying the cells is aspirated. Cells then are washed with PBS, pH 2-4 (Gibco/BRL Catalog No. 10010-023) and the PBS is replaced with F12 HAM media containing 5% serum ("selective media"). At 72 hours after transfection, the cells are diluted ten-fold into the selective medium containing the antibacterial agent genetecin at 400 µg/ml (Life Technologies, Catalog No. 11811).

EXAMPLE 3

Agonist Assay

To screen for agonists of human GAVE10, hGAVE10 is coupled artificially to a $G_q$ mechanism. Activation of the $G_q$ mechanism stimulates the release of $Ca^{2+}$ from sarcoplasmic reticulum vesicles within the cell. The $Ca^{2+}$ is released into the cytoplasm where it can be detected using $Ca^{2+}$ chelating dyes. A Fluorometric Imaging Plate Reader or FLIPR® apparatus (Molecular Devices) is used to monitor any resulting changes in fluorescence. The activity of an agonist is reflected by any increase in fluorescence.

CHO-K1 cells expressing hGAVE10 are pre-engineered to express an indiscriminate form of $G_q$ protein ($G_{\alpha 16}$). To prepare such cells, $G_{\alpha 16}$-coupled CHO cells are obtained commercially (Molecular Devices LIVEWARE™ cells, Catalog No. RD-HGA16) and the protocol in Example 2 followed to facilitate expression of hGAVE10 in those cells.

The cells are maintained in log phase of growth at 37° C. and 5% $CO_2$ in F12 Ham's media (Gibco/BRL, Catalog No. 11765-054) containing 10% fetal bovine serum, 100 IU/ml penicillin (Gibco/BRL, Catalog No. 15140-148), 100 µg/ml streptomycin (Catalog No. 15140-148, Gibco/BRL), 400 µg/ml genetecin (G418) (Gibco/BRL, Catalog No. 10131-035) and 200 µg/ml zeocin (Invitrogen, Catalog No. R250-05). One day prior to an assay, 12,500 cells/well of the CHO-K1 cells are plated onto 384-well clear-bottomed assay plates with a well volume of 50 µl (Greiner/Marsh, Catalog No. N58102) using a 96/384 Multidrop device (Labsystems, Type 832). The cells are incubated at 37° C. in a humidified 5% $CO_2$ incubator (Forma Scientific $CO_2$ water-jacketed incubator Model 3110).

The following stock solutions are prepared: a 1 M stock solution of Hepes (pH 7.5) (Gibco/BRL, Catalog No. 15630-080); a 250 mM stock solution of probenicid (Sigma, Catalog No. P8761) made in 1 N NaOH; and a 1 mM stock solution of Fluo 4-AM Dye (Molecular Probes, Catalog No. Fl 4202) made in DMSO (Sigma D2650). Reaction buffer is prepared with 1000 ml Hank's balanced salt solution (Fisher/Mediatech, Catalog No. MT21023), 20 ml of the 1 M Hepes stock solution and 10 ml of the 250 mM probenicid stock solution. To prepare the loading buffer, 1.6 ml of the 1 mM Fluo 4-AM Dye stock solution is mixed with 0.32 ml of pluronic acid (Molecular Probes, Catalog No. P6866) and then mixed with 400 ml of the above reaction buffer and 4 ml of fetal bovine serum.

One hour prior to the assay, 50 µl of freshly-prepared loading buffer is added to each well of the 384-well plate using a 96/384 Multidrop device. The cells are incubated at 37° C. in a humidified incubator to maximize dye uptake. Immediately prior to the assay, the cells are washed 2 times with 90 µl of reaction buffer using a 384 EMBLA Cell Washer (Skatron; Model No. 12386) with the aspiration head set at least 10 mm above the plate bottom, leaving 45 µl of buffer per well.

The CCD camera (Princeton Instruments) of the FLIPR® II (Molecular Devices) instrument is set at an f-stop of 2.0 and an exposure of 0.4 seconds. The camera is used to monitor the cell plates for accuracy of dye loading.

A compound library containing possible agonists is tested at a concentration of 10 µM in physiological salt buffer. Changes in fluorescence are measured for 10 seconds prior to compound addition. After the addition of the compound, fluorescence is measured every second for the first minute followed by exposures taken every six seconds for a total experimental analysis time of three minutes. Five µl aliquots of the 100 µM stock compound are added after the tenth scan, giving a final compound concentration on the cells of 10 µM. The maximum fluorescence changes for the first 80 scans are recorded as a measure of agonist activity and compared to the maximum fluorescence change induced by 10 µM ATP (Sigma A9062).

EXAMPLE 4

Antagonist Assay

To screen for antagonists of human GAVE10, hGAVE10 is coupled artificially to a $G_q$ mechanism. As in Example 3, a FLIPR® apparatus is used to monitor any resulting changes in fluorescence. The activity of an antagonist is reflected by any decrease in fluorescence.

CHO-K1 cells expressing hGAVE10 are pre-engineered to express an indiscriminate form of $G_q$ protein ($G_{\alpha 16}$), as described in Example 3. The cells are maintained in log phase of growth at 37° C. and 5% $CO_2$ in F12 HAM media (Gibco/BRL, Catalog No. 11765-054) containing 10% fetal bovine serum, 100 IU/ml penicillin (Gibco/BRL, Catalog No. 15140-148), 100 µg/ml streptomycin (Catalog No. 15140-148, Gibco/BRL), 400 µg/ml genetecin (G418) (Gibco/BRL, Catalog No. 10131-035) and 200 µg/ml zeocin (Invitrogen, Catalog No. R250-05). One day prior to the assay, 12,500 cells/well of the CHO-K1 cells are plated onto 384-well black/clear bottomed assay plates with a well volume of 50 µl (Greiner/Marsh, Catalog No. N58102) using a 96/384 Multidrop device. The cells are allowed to incubate at 37° C. in humidified 5% $CO_2$.

The following stock solutions are prepared: a 1 M stock solution of Hepes (pH 7.5) (Gibco/BRL, Catalog No. 15630-080); a 250 mM stock solution of probenicid (Sigma, Catalog No. P8761) made in 1 N NaOH; a 1 mM stock solution of Fluo 4-AM Dye (Molecular Probes, Catalog No. F 14202) made in DMSO (Sigma D2650); and a stock solution of ligand or antagonist. Reaction buffer is prepared with 1000 ml Hank's balanced salt solution (Fisher/Mediatech, Catalog No. MT21023), 20 ml of the 1 M Hepes stock solution, 10 ml of the 250 mM probenicid stock solution and 1 mM $CaCl_2$. To prepare the loading buffer, 80 µl of the 1 mM Fluo 4-AM Dye stock solution is mixed with 16 µl of pluronic acid (Molecular Probes, Catalog No. P6866) and then mixed with 20 ml of the above reaction buffer and 0.2 ml of fetal bovine serum.

Thirty minutes prior to the assay, 30 µl of freshly-prepared loading buffer is added to each well of the 384-well plate using a 96/384 Multidrop device. The cells are incubated at 37° C. in a humidified $CO_2$ incubator to maximize dye uptake. Immediately prior to the assay, the cells are washed 3 times with 100 µl of reaction buffer using a 384 EMBLA Cell Washer with the aspiration head set at least 40 mm above the plate bottom, leaving 45 µl of buffer per well.

Five µl of the 100 µM stock antagonist compound are added to the cells using a Platemate-384 pipettor (Matrix). The compound concentration during the incubation step is approximately 10 µM. The cells are placed on the FLIPR® II and plate fluorescence is measured every second for the first minute followed by exposures taken every six seconds for a total experimental analysis time of three minutes. Antagonist or ligand (10 µM) is added after the tenth scan. After each addition, the 384 tips are washed 10 times with 20 µl of 0.01% DMSO in water.

EXAMPLE 5

Receptor Binding Assay

To prepare membrane fractions containing hGAVE10 receptor, CHO cell lines overexpressing hGAVE10 are harvested by incubation in phosphate-buffered saline (10 ml) containing 1 mM EDTA. The cells are washed further 3 times in phosphate-buffered saline containing 1 mM EDTA (10 ml) prior to resuspension in 5 ml of Buffer A (50 mM Tris-HCl (pH 7.8) (Sigma T6791), 5 mM $MgCl_2$ (Sigma M8266) and 1 mM EGTA (Sigma 0396).

The cells then are disrupted with a tissue homogenizer (Polytron, Kinemetica, Model PT 10/35) for 1 minute. The resulting homogenate is centrifuged in a Sorvall Instruments RC3B refrigerated centrifuge at 49,000×g at 4° C. for 20 minutes. The resulting pellet is resuspended in 25 ml of Buffer A and the centrifugation step is repeated three times. Following the final centrifugation, the pellet again is resuspended in 5 ml of Buffer A, aliquoted and stored at −70° C.

A receptor binding assay using the membrane fraction and radiolabeled ligand or agonist as a tracer is performed. The assay is performed in a 96-well plate (Beckman Instruments). The binding reaction consists of 18 μg of the CHO cell preparation in the presence of radioactive ligand or agonist (0.01 nM-25 nM) in a final volume of 0.2 ml of Buffer A containing 0.1% bovine serum albumin (Sigma, Catalog No. 34287) (see Im et al., J Biol Chem (2000) 275(19):14281-14286). The reaction is incubated for 1 hour at room temperature. The reaction is terminated by filtration through Whatman GF/C filters on a multichannel harvester (Brandell) that is pretreated with 0.3% polyethyleneimine (Sigma, Catalog No. P3143) and 0.1% bovine serum albumin (BSA) for 1 hour. The mixture is applied to the filter and incubated for one hour. The filters are washed 6 times with 1 ml of ice cold 50 mM Tris-HCl, pH 7.6. Specific binding is calculated based on the difference between total binding and non-specific binding (background) for each tracer concentration by measuring the radioactivity. Eight to 16 concentration data points are obtained to determine the binding of ligand to the receptor achieved in an equilibrium state between the ligand and receptor (equilibrium binding parameters) and the amount of nonradioactive ligand or agonist needed to compete for the binding of radioactive ligand or agonist on the receptor (competition binding values). Inhibition curves are prepared to determine the concentration required to achieve a 50% inhibition of binding ($IC_{50}$).

EXAMPLE 6

Northern Blot Analysis

Northern blot analysis is performed on total RNA or poly $A^+$ RNA derived from several human tissue samples to determine whether the tissues express hGAVE10. The probe used is $P^{32}$-labeled hGAVE10 cDNA or portions thereof.

Preparation of the Probe $P^{32}$-labeled hGAVE10 cDNA is prepared as follows. Twenty-five ng of hGAVE10 cDNA prepared as described above is resuspended to 45 μl of 10 mM Tris-HCl, pH 7.5; 1 mM EDTA in a microfuge tube and heated at 95° C. for 5 minutes. The tube then is chilled on ice for another 5 minutes. Following chilling, the mixture contained in the tube is resuspended with the 45 μl GAVE10 cDNA and buffer as described above and mixed with RTS Rad Prime Mix (supplied with the RTS Rad Prime DNA-labeling System) (Life Technologies, Catalog No. 10387-017). Five μl of $P^{32}$-labeled α-dCTP, specific activity 3000 Ci/mM, (Amersham, AA0005), are added while mixing gently but thoroughly. The resulting mixture is incubated at 37° C. for 10 minutes. Incubation is stopped by the addition of 5 μl of 0.2 M EDTA, pH 8.0. Incorporation of the radioactive α-dCTP into the hGAVE10 cDNA is evaluated by taking a 5 μl aliquot of the mixture and counting the radioactivity.

RNA Extraction

Cells of interest are lysed directly in a culture dish by adding 1 ml of Trizol Reagent (Life Technologies, Catalog No. 15596). The cell lysate then is passed through a pipette several times to homogenize the lysate (cell lysate subsequently is transferred to a tube). Following homogenization, the lysate is incubated for 5 minutes at 30° C. to permit the complete dissociation of nucleoprotein complexes. Following incubation, 0.2 ml of chloroform (Sigma, Catalog No. C53 12) per 1 ml of Trizol Reagent are added to the lysate and the tube is shaken vigorously for 15 seconds. The lysate then is incubated at 30° C. for 3 minutes. Following incubation, the lysate is centrifuged at 12,000×g for 15 minutes at 4° C. The resulting aqueous phase is transferred to a fresh tube and 0.5 ml of isopropyl alcohol per 1 ml of Trizol Reagent are added. The aqueous phase sample then is incubated at 30° C. for 10 minutes and centrifuged at 12,000×g for 10 minutes at 4° C. Following centrifugation, the supernatant is removed and the remaining RNA pellet is rinsed with 70% ethanol. The rinsed sample then is centrifuged at 7500×g for 10 minutes at 4° C. and the resulting supernatant is discarded. The remaining RNA pellet then is dried and resuspended in RNase-free water (Life Technologies, Catalog No. 10977-015). Either total RNA, for example the samples from peripheral tissues, or poly $A^+$ RNA, such as the samples of various brain regions, can be used in the Northern or Taqman (described below) experiments. Known standards, such as human brain actin of Perkin-Elmer, can be purchased.

Gel Electrophoresis

An agarose gel is prepared by melting 2 g of agarose (Sigma, Catalog No. A0169) in water, 5× formaldehyde gel-running buffer (see below for description) and 2.2 M formaldehyde (Sigma, Catalog No. P82031).

Samples for Gel Electrophoresis were Prepared as Follows:

| | |
|---|---|
| RNA | 4.5 μl (5 μg total) |
| 5X formaldehyde gel-running buffer | 2.0 μl |
| formaldehyde | 3.5 μl |
| formamide (Sigma, Catalog No. F9037) | 10.0 μl |

Formaldehyde gel-running buffer (5×) is 0.1 M 3-(N-morpholino) propanesulfonic acid (MOPS) (pH 7.0) (Sigma, Catalog No. M5162); 40 mM sodium acetate (Sigma, Catalog No. S7670); and 5 mM EDTA (pH 8.0) (Sigma, Catalog No. E7889).

The samples are incubated for 15 minutes at 65° C. and then chilled on ice. After chilling, the samples are centrifuged for 5 seconds. Two μl of formaldehyde gel-loading buffer; 50% glycerol (Sigma, Catalog No. G5516); 1 mM EDTA (pH 8.0); 0.25% bromophenol blue (Sigma, Catalog No. 18046); 0.25% xylene cyanol FF (Sigma, Catalog No. 335940) then are added to the sample.

Table 1 lists the sources of some of the RNA's used in some of the experiments.

TABLE 1

| Human Total RNA | Clontech Cat. No. |
|---|---|
| Human brain, whole | 64020-1 |
| Human Heart | 64025-1 |
| Human Kidney | 64030-1 |
| Human Liver | 64022-1 |
| Human Lung | 64023-1 |
| Human Pancreas | 64031-1 |
| Human Skeletal Muscle | 64033-1 |
| Human Small Intestine | 64039-1 |
| Human Spleen | 64034-1 |
| Human Stomach | 64090-1 |
| Human Thymus | 64028-1 |

The gel is pre-run for 5 minutes at 5 V/cm. Following the pre-run; the samples are loaded onto the gel. The gel then is run at 4 V/cm while submerged in 1× formaldehyde gel-running buffer. The buffer is changed at 2 hours into the run.

Transfer of RNA from Gel to Nitrocellulose

The gel is stained with ethidium bromide (Sigma, Catalog No. El 385) (0.5 µg/ml in 0.1 M ammonium acetate (Sigma, Catalog No. 09689)) for 30 minutes to insure that RNA is not degraded. The RNA then is transferred from the agarose gel to a nitrocellulose filter (Schleicher & Schuell Inc., Catalog No. 74330-026) using the protocol described in Sambrook et al., eds. (in Molecular Cloning: A Laboratory Manual, volume 1, pp.7.46-7.51, Cold Spring Harbor Laboratory Press (1989)).

Hybridization of $P^{32}$-Labeled cDNA

Clontech ExpressHyb hybridization solution (Clontech, Catalog No. 8015-1) is incubated at 68° C. for 2 hours. Following incubation, 15 ml of the warmed hybridization solution is poured onto a multiple tissue sample Northern (MTN) membrane. The MTN membrane is left soaking in the hybridization solution at 68° C. while shaking. After 1 hour elapsed, the hGAVE10 cDNA probe, that had been previously denatured by boiling at 95° C. for 5 minutes, is added at a concentration of $10^6$ counts/ml. The incubation of the hybridization solution covering the gel at 68° C. then is continued for 2 hours while shaking.

The MTN membrane then is removed from the Clontech ExpressHyb hybridization solution and washed 3 consecutive times with Clontech Wash Solution 1 (2×SSC; 0.05% SDS) by dipping the membrane into 15 ml of solution while shaking at room temperature for 40 minutes, respectively, with solution changes every 40 minutes. Clontech Wash Solution 2 (0.1×SSC; 0.1% SDS) then is warmed at 55° C. for 1 hour. The membrane then is washed 3 consecutive times with Clontech Wash Solution 2 (0.1×SSC; 0.1% SDS) by dipping the membrane into 15 ml of solution while shaking at 55° C. temperature for 60 minutes. The wash solution is changed every 15 minutes.

Development

The membrane is exposed to Kodak X-OMAT AR (Kodak, Catalog No. 165 1579) film overnight at −70° C. and developed by standard methods. A number of different tissues were screened and a unique mRNA of about 2.3 kb was found in selected tissues, such as, spleen and lung.

EXAMPLE 7

PCR Assay

TaqMan® or real time RT-PCR detects messenger RNA in samples. The assay exploits the 5' nuclease activity of AmpliTaq Gold® DNA polymerase to cleave a TaqMan® probe during PCR. The TaqMan® probe contains a reporter dye for example, 6-FAM (6-carboxyfluorescein) at the 5'-end of the probe and a quencher dye (for example, TAMRA (6-carboxy-N,N,N',N'-tetramethylrhodamine) at the 3'-end of the probe. TaqMan® probes are designed specifically to hybridize with the target cDNA of interest between the forward and the reverse primer sites. When the probe is intact, the 3'-end quencher dye suppresses the fluorescence of the 5'-end reporter dye. During PCR, the 5'→3' activity of the AmpliTaq Gold® DNA polymerase results in the cleavage of the probe between the 5'-end reporter dye and the 3'-end quencher dye resulting in the displacement of the reporter dye. Once displaced, the fluorescence of the reporter dye no longer is suppressed by the quencher dye. Thus, the accumulation of PCR products made from the targeted cDNA template is detected by monitoring the increase in fluorescence of the reporter dye.

An ABI Prism Sequence detector system from Perkin Elmer Applied Biosystems (Model No. ABI7700) is used to monitor the increase of the reporter fluorescence during PCR. The reporter signal is normalized to the emission of a passive reference.

Preparation of cDNA Template

Total RNA and poly A⁺ RNA from several tissues can be purchased commercially, for example, from Clontech (see Table 1 above and Table 2 below).

TABLE 2

| RNA Sample | Clontech Catalog No. |
|---|---|
| Human Brain, whole | 6516-1 |
| Human Brain, amygdala | 6574-1 |
| Human Brain, caudate nucleus | 6575-1 |
| Human Brain, cerebellum | 6543-1 |
| Human Brain, corpus callosum | 6577-1 |
| Human Brain, hippocampus | 6578-1 |
| Human Brain, substantia nigra | 6580-1 |
| Human Brain thalamus | 6582-1 |
| Human Fetal Brain | 6525-1 |

Five µg of total RNA is mixed with 2 µl (50 ng/µl) of random hexamer primers (Life Technologies, Catalog No. 18090) for a total reaction volume of 7 µl. The resulting mixture is heated at 70° C. for 10 minutes and quickly chilled on ice. The following then are added to the mixture: 4 µl of 5×first strand buffer, 2 µl of 0.1 mM DTT, 1 µl of 10 mM dNTP and 1 µl of water. The mixture is mixed gently and incubated at 37° C. for 2 minutes. Following the incubation, 5 µl of Superscript RT-PCR reverse transcriptase (Life Technologies, Catalog No. 18090) is added. The mixture then is incubated at 37° C. for 60 minutes. The reaction is stopped by the addition of 1 µl of 2.5 mM EDTA. The mixture then is incubated for 65° C. for 10 minutes.

PCR and TaqMan® Assay

The PCR and TaqMan® Assay are performed in a 96-well plate MicroAmp optical tube (Perkin Elmer, Catalog No. N801-0933). A reaction mixture comprising 25 µl of TaqMan® PCR Mixture (Perkin Elmer, Catalog No. N808-0230), 1 µl forward primer (5'-TGCTCTTTGCCAGTCT-GCC-3') (SEQ ID NO:10), 1 µl of reverse primer (5'-AAGATAGCCTGGGAGCTGCA-3') (SEQ ID NO:11), 1 µl of TaqMan® probe (5'-TGGAACCACTGGACCCCTG-GTGC-3') (SEQ ID NO:12), 1 µl cDNA and 21 µl of water are placed into each well. TaqMan® samples are created in duplicate for each tissue sample at the following cDNA template concentrations: 5, 2, 1, 0.5, 0.25, 0.125, 0.0625 ng/µl (the template cDNA concentration is a final concentration). The plate then is sealed with MicroAmp optical 8-strip caps (Perkin Elmer, Catalog No. N801-0935).

A standard curve is performed in duplicate using the human β actin gene (Perkin Elmer, Catalog No. 401846). For each cDNA template concentration of the standard curve, a number of amplified molecules were obtained. Having a standard curve amplification of a known gene allows for quantification of cDNA molecules amplified for each unknown target gene and normalization with an internal control.

Results from the above TaqMan® reactions are expressed relative to a tissue of arbitrary choice as fold regulation (for instance, value of GAVE10 expression in the spleen divided by the value of GAVE10 expression in the brain). Alternatively, a different tissue of known reactivity can be used as the frame of reference, such as β actin. High levels of GAVE10 mRNA were observed.

EXAMPLE 7

Identification of Inverse Agonist and Agonist Using [$^{35}$S]GTPγS.

Membranes comprising the constitutively active receptors are prepared by first aspirating the media from a confluent monolayer of eukaryotic cells expressing GAVE10 (cells may be in a flask or multi-welled plate), followed by rinsing with 10 ml of cold PBS and further aspiration. Five ml of a buffer containing 20 mM HEPES and 10 mM EDTA, pH 7.4 are added to scrape the cells from the substratum. The cellular material is transferred into 50 ml centrifuge tubes (centrifuge at 20,000 rpm for 17 minutes at 4° C.). Thereafter the supernatant is aspirated and the resulting pellet is resuspended in 30 ml of a buffer containing 20 mM HEPES and 0.1 mM EDTA, pH 7.4, which is followed by centrifugation as above. The supernatant then is aspirated and the resulting pellet is resuspended in a buffer containing 20 mM HEPES, 100 mM NaCl and 10 mM $MgCl_2$ (binding buffer). The suspension then is homogenized using a Brinkman polytron® homogenizer (15-20 second bursts until all the material is in a uniform suspension) to produce a membrane protein preparation. Protein concentration is determined by the Bradford method (see WO 00/22131).

Candidate compounds preferably are screened using a 96-well plate format. Membrane protein preparations are diluted to 0.25 mg/ml in binding buffer to provide a final concentration of 12.5 μg/well in a 50 μl volume. One hundred μl of GDP buffer (37.5 ml of binding buffer and 2 mg GDP, Sigma Cat. No. G-7127) are added to each well followed by addition of a Wallac Scintistrip™ (Wallac). Five ill of a candidate compound are transferred into each well (i.e., 5 μl in a total assay volume of 200 μl resulting in a 1:40 ratio such that the final concentration of candidate is 10 μM). Fifty μl of membrane protein are added to each well (including a non-receptor containing membrane control) and pre-incubation is carried out for 5-10 minutes at room temperature. Thereafter, 50 μl of [$^{35}$S]GTPγS (0.6 nM) in binding buffer are added to each well, followed by incubation on a shaker for 60 minutes at room temperature. The assay is stopped by spinning the plates at 4,000 rpm for 15 minutes at 22° C. The plates then are aspirated with an 8 channel manifold, sealed with plate covers and read on a Wallac 1450™ using setting "Prot.#37" (as per manufacturer's instructions). Changes in the amount of material bound to the strips will determine whether the candidate is an inverse agonist (decrease relative to base line) or agonist (increase relative to base line).

Although the instant invention has been described in detail with reference to the examples above, it is understood that various modifications can be made without departing from the spirit of the invention. Accordingly, the invention is limited only by the following claims. All cited patents and publications referred to in the application herein are incorporated by reference in entirety.

We claim:

1. An isolated nucleic acid molecule comprising the nucleic acid sequence of SEQ ID NO:1.

2. The isolated nucleic acid molecule of claim 1, wherein the nucleic acid encodes the polypeptide of SEQ ID NO:2.

3. The isolated nucleic acid molecule of claim 1, further comprising a detectable label.

4. The isolated nucleic acid molecule of claim 3, wherein the detectable label comprises an enzyme, a radioactive isotope, or a chemical which fluoresces.

5. The isolated nucleic acid molecule of claim 1, wherein the nucleic acid sequence is selected from the group consisting of RNA, synthetic RNA, genomic DNA, synthetic DNA, and cDNA.

* * * * *

SEQUENCE LISTING

<160> NUMBER OF SEQ ID NOS: 12

<210> SEQ ID NO 1
<211> LENGTH: 1586
<212> TYPE: DNA
<213> ORGANISM: Homo sapiens

<400> SEQUENCE: 1

```
ccttagacgt ggttcaaagt ttttttcttc ctttcaggtg tcgtgaaaag cttgaattcg      60
gcgcgccaga tatcacacgt gccaaggggc tggctcagga gagcctggcc ccgctgtccc     120
cactgggtgg agacaccatg cacttggtcc acttgtgctc ttcagccagg acaccagaca     180
tggtccaaac cgctgcaggg ctggctgcag caactccctg acactcagga aggcccaggc     240
tgggcaggca atacctgctc ccaacagcca tgcatgccga ctgccgctcc aggactcccc     300
tgtccccagg accaagatga cgcccaacag cactggcgag gtgcccagcc ccattcccaa     360
gggggctttg gggctctccc tggccctggc aagcctcatc atcaccgcga acctgctcct     420
agccctgggc atcgcctggg accgccgcct gcgcagccca cctgctggct gcttcttcct     480
gagcctactg ctggctgggc tgctcacggg tctggcattg cccacattgc cagggctgtg     540
gaaccagagt cgccgggtt actggtcctg cctcctcgtc tacttggctc caacttctc      600 cttcctctcc ctgcttgcca acctcttgct ggtgcacggg gagcgctaca tggcagtcct     660
```

```
gaggccactc cagcccctg ggagcattcg gctggccctg ctcctcacct gggctggtcc      720
cctgctcttt gccagtctgc ccgctctggg gtggaaccac tggacccctg gtgccaactg      780
cagctcccag gctatcttcc cagcccccta cctgtacctc gaagtctatg gctcctgct       840 gcccgccgtg ggtgctgctg ccttcctctc tgtccgcgtg ctggccactg cccaccgcca      900
gctgcaggac atctgccggc tggagcgggc agtgtgccgc gatgagccct ccgccctggc      960
ccgggccctt acctggaggc aggcaagggc acaggctgga gccatgctgc tcttcgggct     1020
gtgctggggg ccctacgtgg ccacactgct cctctcagtc ctggcctatg agcagcgccc     1080
gccactgggg cctgggacac tgttgtccct cctctcccta ggaagtgcca gtgcagcggc     1140
agtgcccgta gccatggggc tgggcgatcg cgctacaca gcccctgga gggcagccgc       1200 ccaaaggtgc ctgcaggggc tgtggggaag agcctcccgg acagtcccg gccccagcat      1260 tgcctaccac ccaagcagcc aaagcagtgt cgacctggac ttgaactaaa ggaagggcct     1320
ctgctgactc ctaccagagc atccgtccag ctcagccatc cagcctgtct ctactgggcc     1380
ccacttctct ggatcagaga ccctgcctct gtttgacccc gcactgactg aataaagctc     1440
ctctggccgt taaaaaaaaa aaaaaaaaaa aaaaaaaaaa aaaaaaaaa aaaaaaaca       1500 ttacctcttt ctccgcacct ggcctgcagg cggccgcagg taagccagcc caggcctcgc     1560
cctccagctc aaggcgggac aggtgc                                          1586
```

<210> SEQ ID NO 2
<211> LENGTH: 330
<212> TYPE: PRT
<213> ORGANISM: Homo sapiens

<400> SEQUENCE: 2

```
Met Thr Pro Asn Ser Thr Gly Glu Val Pro Ser Pro Ile Pro Lys Gly
1               5                   10                  15

Ala Leu Gly Leu Ser Leu Ala Leu Ala Ser Leu Ile Ile Thr Ala Asn
            20                  25                  30

Leu Leu Ala Leu Gly Ile Ala Trp Asp Arg Arg Leu Arg Ser Pro
        35                  40                  45

Pro Ala Gly Cys Phe Phe Leu Ser Leu Leu Ala Gly Leu Leu Thr
    50                  55                  60

Gly Leu Ala Leu Pro Thr Leu Pro Gly Leu Trp Asn Gln Ser Arg Arg
65                  70                  75                  80

Gly Tyr Trp Ser Cys Leu Leu Val Tyr Leu Ala Pro Asn Phe Ser Phe
                85                  90                  95

Leu Ser Leu Leu Ala Asn Leu Leu Leu Val His Gly Glu Arg Tyr Met
            100                 105                 110

Ala Val Leu Arg Pro Leu Gln Pro Pro Gly Ser Ile Arg Leu Ala Leu
        115                 120                 125

Leu Leu Thr Trp Ala Gly Pro Leu Leu Phe Ala Ser Leu Pro Ala Leu
    130                 135                 140

Gly Trp Asn His Trp Thr Pro Gly Ala Asn Cys Ser Ser Gln Ala Ile
145                 150                 155                 160

Phe Pro Ala Pro Tyr Leu Tyr Leu Glu Val Tyr Gly Leu Leu Leu Pro
                165                 170                 175

Ala Val Gly Ala Ala Ala Phe Leu Ser Val Arg Val Leu Ala Thr Ala
            180                 185                 190

His Arg Gln Leu Gln Asp Ile Cys Arg Leu Glu Arg Ala Val Cys Arg
        195                 200                 205
```

-continued

```
Asp Glu Pro Ser Ala Leu Ala Arg Ala Leu Thr Trp Arg Gln Ala Arg
    210                 215                 220

Ala Gln Ala Gly Ala Met Leu Leu Phe Gly Leu Cys Trp Gly Pro Tyr
225                 230                 235                 240

Val Ala Thr Leu Leu Leu Ser Val Leu Ala Tyr Glu Gln Arg Pro Pro
                245                 250                 255

Leu Gly Pro Gly Thr Leu Leu Ser Leu Leu Ser Leu Gly Ser Ala Ser
            260                 265                 270

Ala Ala Ala Val Pro Val Ala Met Gly Leu Gly Asp Gln Arg Tyr Thr
        275                 280                 285

Ala Pro Trp Arg Ala Ala Gln Arg Cys Leu Gln Gly Leu Trp Gly
    290                 295                 300

Arg Ala Ser Arg Asp Ser Pro Gly Pro Ser Ile Ala Tyr His Pro Ser
305                 310                 315                 320

Ser Gln Ser Ser Val Asp Leu Asp Leu Asn
                325                 330

<210> SEQ ID NO 3
<211> LENGTH: 18
<212> TYPE: DNA
<213> ORGANISM: Artificial
<220> FEATURE:
<223> OTHER INFORMATION: primer

<400> SEQUENCE: 3
atgacgccca acagcact                                                  18

<210> SEQ ID NO 4
<211> LENGTH: 18
<212> TYPE: DNA
<213> ORGANISM: Artificial
<220> FEATURE:
<223> OTHER INFORMATION: primer

<400> SEQUENCE: 4
ttagttcaag tccaggtc                                                  18

<210> SEQ ID NO 5
<211> LENGTH: 21
<212> TYPE: DNA
<213> ORGANISM: artificial
<220> FEATURE:
<223> OTHER INFORMATION: antisense

<400> SEQUENCE: 5
ctgttgggcg tcatcttggt c                                              21

<210> SEQ ID NO 6
<211> LENGTH: 21
<212> TYPE: DNA
<213> ORGANISM: artificial
<220> FEATURE:
<223> OTHER INFORMATION: primer

<400> SEQUENCE: 6
caggaccaaa tgacgacgcc a                                              21

<210> SEQ ID NO 7
<211> LENGTH: 24
<212> TYPE: DNA
<213> ORGANISM: artificial
<220> FEATURE:
```

```
<223> OTHER INFORMATION: primer

<400> SEQUENCE: 7
cgaagcttca ggaccaagat gagc                                              24

<210> SEQ ID NO 8
<211> LENGTH: 18
<212> TYPE: DNA
<213> ORGANISM: artificial
<220> FEATURE:
<223> OTHER INFORMATION: t7forward primer

<400> SEQUENCE: 8
ggctcccssc ttctcttc                                                     18

<210> SEQ ID NO 9
<211> LENGTH: 18
<212> TYPE: DNA
<213> ORGANISM: artificial
<220> FEATURE:
<223> OTHER INFORMATION: M13 reverse primer

<400> SEQUENCE: 9
gggcagtggc cagcacgc                                                     18

<210> SEQ ID NO 10
<211> LENGTH: 19
<212> TYPE: DNA
<213> ORGANISM: artificial
<220> FEATURE:
<223> OTHER INFORMATION: primer

<400> SEQUENCE: 10
tgctctttgc cagtctgcc                                                    19

<210> SEQ ID NO 11
<211> LENGTH: 20
<212> TYPE: DNA
<213> ORGANISM: artificial
<220> FEATURE:
<223> OTHER INFORMATION: primer

<400> SEQUENCE: 11
aagatagcct gggagctgca                                                   20

<210> SEQ ID NO 12
<211> LENGTH: 23
<212> TYPE: DNA
<213> ORGANISM: artificial
<220> FEATURE:
<223> OTHER INFORMATION: primer

<400> SEQUENCE: 12
tggaaccact ggaccctgg tgc                                                23
```